United States Patent
Honda

(12) 
(10) Patent No.: US 6,468,478 B1
(45) Date of Patent: Oct. 22, 2002

(54) OXYGEN CONCENTRATION SENSOR ELEMENT IMPEDANCE DETECTING APPARATUS AND METHOD

(75) Inventor: Takayoshi Honda, Nagoya (JP)

(73) Assignee: Denso Corporation, Kariya (JP)

( * ) Notice: Subject to any disclaimer, the term of this patent is extended or adjusted under 35 U.S.C. 154(b) by 0 days.

(21) Appl. No.: 09/348,254

(22) Filed: Jul. 7, 1999

(30) Foreign Application Priority Data

Jul. 13, 1998 (JP) .......................................... 10-197174

(51) Int. Cl.[7] .............................................. G01N 27/04
(52) U.S. Cl. ...................... 422/98; 324/717; 436/139; 327/337; 73/23.32
(58) Field of Search ........................... 422/98; 324/717, 324/464; 204/406, 401, 430; 73/23.32; 436/139; 327/337

(56) References Cited

U.S. PATENT DOCUMENTS

| | | | |
|---|---|---|---|
| 4,178,793 A | * 12/1979 | Bremer et al. .................. | 73/23 |
| 4,576,705 A | * 3/1986 | Kondo et al. ................ | 204/406 |
| 4,626,338 A | * 12/1986 | Kondo et al. ................ | 204/406 |
| 5,547,552 A | * 8/1996 | Hasegawa et al. .......... | 204/406 |
| 5,554,951 A | * 9/1996 | Gough ....................... | 327/337 |
| 5,672,258 A | * 9/1997 | Greenblatt et al. ......... | 204/430 |
| 5,965,451 A | * 10/1999 | Plog et al. .................. | 436/139 |
| 5,967,129 A | * 10/1999 | Yamashita et al. .......... | 123/674 |
| 5,974,857 A | * 11/1999 | Yamashita et al. ......... | 73/23.32 |
| 6,084,418 A | * 7/2000 | Takami et al. ............... | 324/717 |
| 6,120,663 A | * 9/2000 | Kato et al. ................... | 204/401 |
| 6,160,404 A | * 12/2000 | Schenk ........................ | 324/464 |

FOREIGN PATENT DOCUMENTS

JP 9-292364 11/1997

* cited by examiner

*Primary Examiner*—Jill Warden
*Assistant Examiner*—Brian Sines
(74) *Attorney, Agent, or Firm*—Nixon & Vanderhye P.C.

(57) ABSTRACT

An oxygen concentration sensor element impedance detecting apparatus and method that maintains sensor detection accuracy by shortening the sweeping time period of an element impedance detecting voltage. A sub-microcomputer performs at least two sweeping actions for switching an element application voltage Vo from a reference voltage to a sweeping voltage when it once detects the element impedance of the oxygen concentration sensor AFS, and A/D converts only one of the element application voltage Vo and an element current detecting voltage Vi during the sweep, to shorten the sweeping time period. A sensor drive circuit prevents the element application voltage Vo from being changed by the element current. Even if element application voltage Vo detection and element current detecting voltage Vi detection are performed by separate sweeps, detection results substantially identical to those of the case in which detection of those two voltages are performed during one sweep are obtained.

18 Claims, 18 Drawing Sheets

OXYGEN CONCENTRATION SENSOR ELEMENT IMPEDANCE DETECTING APPARATUS AND METHOD

CROSS-REFERENCE TO RELATED APPLICATION

The present application is related to, and claims priority in, Japanese Patent Application No. Hei. 10-197174, the contents of which are incorporated herein by reference.

BACKGROUND OF THE INVENTION

1. Field of the Invention

The present invention relates to impedance detecting apparatuses, and particularly to an apparatus for detecting the element impedance of an oxygen concentration sensor.

2. Discussion

In conventional vehicle air/fuel ratio control systems, catalyst exhaust gas purifying performance is enhanced by detecting the oxygen concentration in the exhaust gas with an oxygen concentration sensor. Based on the detected value, the air/fuel ratio of the mixture to be sucked into the engine may be feedback-controlled. Since the oxygen concentration sensor output voltage generally is highly dependent on temperature, the element temperature has to be kept at a proper level to maintain the detection accuracy of the sensor.

Therefore, some oxygen concentration sensors are equipped with a heater, the energization of which is feedback-controlled to keep the element temperature at or above the activation temperature (e.g., about 600° C. or higher). In this system, the element temperature has to be detected for feedback control of the heater energization. However, the temperature sensor increases the size of the oxygen concentration sensor and increases the associated system cost.

Due to the fact that the sensor element impedance changes with the element temperature, it has been proposed to compute the element temperature from an element impedance by detecting the latter. Unexamined Published Japanese Patent Application No. Hei. 9-292364 discloses a method for detecting element impedance. In this method, an element application voltage Vo is switched from a reference voltage at the oxygen concentration detecting time to a sweeping voltage for detecting the element impedance so that the element impedance is detected from a voltage change $\Delta$Vo at that time and a voltage change $\Delta$Vi according to a current change in response to the voltage change $\Delta$Vo.

In the oxygen concentration sensor system, an element current detecting voltage Vi according to the element current (or oxygen concentration) and the element application voltage Vo are fetched for a constant sampling period (e.g., period of 4 ms) by a microcomputer through the A/D converter to detect the oxygen concentration and accordingly the element impedance. Immediately-before the element application voltage Vo is to be swept to a sweeping voltage, as shown in FIG. 18, the element application voltage Vo and the element current detecting voltage Vi are sequentially A/D-converted twice during the sweep. Since one A/D conversion takes a time period of 50 $\mu$s, for example, an A/D conversion time period of at least 100 $\mu$s is required during the sweep if two A/D conversions are made during the sweep.

In the practical system, channel signals other than the voltages Vo and Vi may be A/D converted during the sweep, and the A/D conversions of the voltages Vo and Vi may be delayed during the sweep by the A/D conversions of the other channel signals. It is therefore necessary to retain the time period for the A/D conversion to some extent. On the other hand, the period for detecting the oxygen concentration is preferably set to a short value (e.g., a period of 4 ms) to improve the detection responsiveness to the change in the oxygen concentration.

After the sweeping time period lapses, to converge the element current quickly into an ordinary state, the element application voltage Vo is switched to a return voltage deviated to the opposite side from the reference voltage by the difference between the reference and sweeping voltages. This deviation promotes the release of the charge stored in the sensor element during the sweep and latches the return voltage for the same time period as the sweeping time period. The element application voltage Vo is returned to the reference voltage at the instant when the charge stored by the capacity component of the element is released. If the sweeping time period is set long considering that the A/D conversions of the two voltages Vo and Vi during the sweep are delayed by the A/D conversions of the other channel signals, the return time period has to be accordingly increased to delay the more the element application voltage Vo to the reference voltage after the sweep. As a result, before the element application voltage Vo returns from the return voltage to the reference voltage, the timing of the A/D conversions of the next voltages Vo and Vi may arrive, and the voltage Vi according to the element current (or oxygen concentration) may not be accurately detected. Such inaccurate detection thereby compromises the detection accuracy of the oxygen concentration. If the sweeping time period is shortened to avoid this problem, the A/D conversions of the other channel signals cannot be made during the sweep.

SUMMARY OF THE INVENTION

Therefore, it is an object of the present invention to provide an oxygen concentration sensor element impedance detecting apparatus that shortens the sweeping time period for detecting the element impedance of the oxygen concentration sensor to detect the oxygen concentration with a high degree of accuracy without being influence by the sweep, and that -performs the A/D conversion of the signal to be used in subsequent control during the sweep.

More particularly, with an oxygen concentration sensor element impedance detecting apparatus according to the present invention, at least two sweeping operations are performed to switch the element application voltage from the reference voltage to the sweeping voltage when the element impedance is detected. Thus, the detection (or A/D conversion) of the element application voltage and the detection (or A/D conversion) of the element current detecting voltage can be performed during the different sweeping time periods.

Therefore, the element application voltage is controlled so as not to be changed by the element current (or oxygen concentration), so that detection results substantially identical to those when the detection of the element application and element current detecting voltages are made for one sweep can be obtained even if the detection of the two voltages are made for different sweeps. On the basis of these detection results, the element impedance is detected.

As a result, only one of the element application voltage and the element current detecting voltage need be detected for one sweep, so that the sweeping time period can be accordingly made shorter than that of conventional impedance detecting apparatuses. Thus, oxygen concentration can be accurately detected without any influence from the sweep, and the signals to be used for another control during the sweep can be A/D converted.

DETAILED DESCRIPTION OF THE PREFERRED EMBODIMENTS

FIGS. 1–7 show an embodiment of the present invention applied to an air/fuel ratio control system. An oxygen concentration sensor AFS is a threshold current-type oxygen concentration sensor (or an air/fuel ratio sensor) and is located in the exhaust passage of an engine to generate a threshold current substantially proportional to the oxygen concentration (or air/fuel ratio) in the exhaust gas. This oxygen concentration sensor AFS has a high activation temperature (about 600° C. or higher) and a narrow activation temperature range that cannot be maintained with only the heat of the exhaust gas. Therefore, this sensor AFS is equipped with a heater 51, the energization of which is subjected to feedback control so that the element temperature of the sensor AFS is maintained within the activation temperature range. As will be described hereinafter, at this time, an element impedance is detected based on the element temperature of the oxygen concentration sensor AFS.

Figure 1:
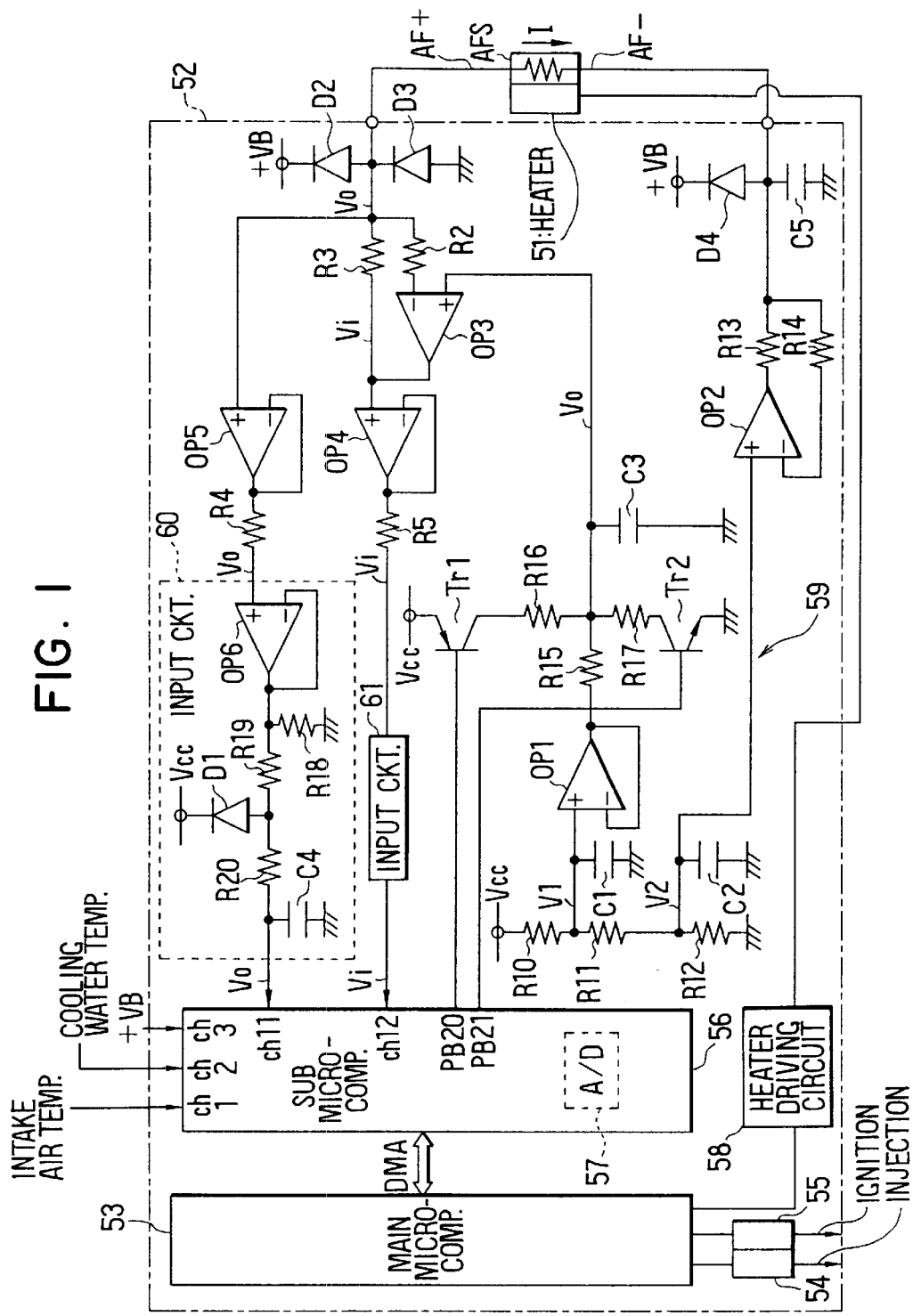
FIG. 1 is an electric circuit diagram showing a circuit of an oxygen concentration detecting system of a first embodiment of the invention.

With reference to FIG. 1, the construction of an oxygen concentration detecting system 52 will be described. A main microcomputer 53 controls engine ignition and injection functions by outputting ignition and injection command signals according to ignition/injection control programs stored in the (not-shown) ROM thereof, to the igniter and fuel injection valve (not shown) through drive circuits 54, 55. A sub-microcomputer 56 is attached to the microcomputer 53 to transfer the data by DMA (Direct Memory Access).

This sub-microcomputer 56 has an A/D converter 57 for A/D converting the battery voltage (+VB), the cooling water temperature and the intake air temperature, as fetched from input ports ch1, ch2 and ch3, to transfer the converted data to the main microcomputer 53. The sub-microcomputer 56 outputs a signal for switching the element application voltage Vo of the oxygen concentration sensor a AFS from the output ports PB20, PB21 to the transistors Tr1, Tr2 of a sensor drive circuit 59.

This sub-microcomputer 56 executes the later-described interrupt routine of FIGS. 5 and 6, as stored in its ROM, to fetch the element application voltage Vo and an element current detecting voltage Vi of the oxygen concentration sensor AFS for a predetermined period (e.g., 4 ms) from input ports ch11, ch12, to A/D convert the voltages via the A/D converter 57 and to compute the oxygen concentration of the exhaust gas based on the A/D converted value. The sub-microcomputer 56 performs the later-described sweeping actions twice for a predetermined period (e.g., 128 ms) to compute the element impedance of the oxygen concentration sensor AFS and to transmit the oxygen concentration and the element impedance to the main microcomputer 53.

On the other hand, the main microcomputer 53 feedback-controls the air/fuel ratio (or fuel injection rate) based on the oxygen concentration of the exhaust gas, as transmitted from the sub-microcomputer 56, and decides the element temperature based on the element impedance of the oxygen concentration sensor AFS, as transmitted from the sub-microcomputer 56. This control enables the main microcomputer to feedback-control the heater 51 through a heater drive circuit 58 thereby to keep the element temperature within the activation temperature range (e.g., about 600° C. or higher).

The construction of the sensor drive circuit 59 for controlling the element application voltage Vo of the will now be described. The supply voltage Vcc is divided by three resistors R10, R11 and R12, and a resulting first voltage V1 (e.g., 3.3 V) and a second voltage V2 (e.g., 3.0 V) are generated and input to the non-inverted input terminals (+) of operation amplifiers OP1, OP2, respectively. Noise eliminating capacitors C1, C2 are connected between the non-inverted input terminals (+) of the individual operation amplifiers OP1, OP2 and ground, respectively.

The output terminal of the operation amplifier OP2, to which the second voltage V2 is input, is connected through a resistor R13 with a minus terminal AF− of the oxygen concentration sensor AFS. The inverted input terminal (−) of the operation amplifier OP2 is connected through a resistor R14 with the minus terminal AF− of the oxygen concentration sensor AFS. As a result, the second voltage V2 (e.g., 3.0 V) to be input to the non-inverted input terminal (+) of the operation amplifier OP2 is applied to the minus terminal AF− of the oxygen concentration sensor AFS.

A noise eliminating and surge absorbing capacitor C5 is connected between the minus terminal AF− of the oxygen concentration sensor AFS and ground (or the minus side of the power supply), and a noise eliminating and surge absorbing diode D4 is connected between the minus terminal AF− and the plus voltage VB of the battery power supply.

The output terminal of the operation amplifier OP1, to which the first voltage V1 is input, is connected through a resistor R15 to the intermediate node between two resistors R16, R17, and the voltage Vo to be generated at the intermediate node is input to the non-inverted input terminal (+) of an operation amplifier OP3. One resistor R16 is connected through the PNP transistor Tr1 to the supply voltage Vcc, and the other resistor R17 is connected through the NPN transistor Tr2 to ground. The individual transistors Tr1, Tr2 are connected at their bases to the output ports PB20, PB21 of the sub-microcomputer 56, respectively, so that they are turned ON/OFF by switching of the output voltages of the output ports PB20, PB21 to high/low levels.

The output terminal of the operation amplifier OP3, to which the voltage Vo is input, is connected through a shunt resistor R3 to the plus terminal AF+ of the oxygen concentration sensor AFS, and the inverted input terminal (−) of the operation amplifier OP3 is connected through a resistor R2 with the plus terminal AF+ of the oxygen concentration sensor AFS. As a result, the voltage Vo to be input to the non-inverted input terminal (+) of the operation amplifier OP3 is applied to the plus terminal AF+ of the oxygen concentration sensor AFS. This voltage Vo is switched by turning ON/OFF the transistors Tr1, Tr2.

More particularly, when no element impedance is being detected (i.e., a normal state of operation), both the transistors Tr1, Tr2 are kept OFF. In this state, the first voltage V1 (at 3.3 V), output from the operation amplifier OP1, is input as a reference voltage to the non-inverted input terminal (+) of the operation amplifier OP3 and is applied to the plus terminal AF+ of the air/fuel ratio sensor AFS.

At a sweeping time, on the other hand, only the ground side transistor Tr2 of the two transistors Tr1 and Tr2 is turned ON. In this state, the voltage (V1−ΔVa), which is prepared by dividing the potential difference (i.e., the first voltage V1) between the first voltage V1 and the ground potential by the resistor R15 and the resistor R17, is input to the non-inverted input terminal (+) of the operation amplifier OP3 so that a voltage (V1−ΔVa) lower by ΔVa than the first voltage V1 is applied to the plus terminal AF+ of the air/fuel ratio sensor AFS. This voltage (V1−ΔVa) is the "sweep voltage".

At a return time after the sweep, only the transistor Tr1 on the side of the supply voltage Vcc of the two transistors Tr1, Tr2 is turned ON. In this state, the voltage (V1+ΔVb), which is prepared by dividing the voltage difference (Vcc−V1) between the supply voltage Vcc and the first voltage V1 by the resistor R16 and the resistor R15, is input to the non-inverted input terminal (+) of the operation amplifier OP3 so that a voltage (V1+ΔVb) higher by ΔVb than the first voltage V1 is applied to the plus terminal AF+ of the air/fuel ratio sensor AFS. This voltage (V1+ΔVb) is the "return voltage".

Here in this embodiment (1), the individual resistors R15, R16 and R17 are set respectively to resistances 200 Ω, 1.5 KΩ and 3.09 KΩ, for example. As a result, for the reference voltage (V1=3.3 V), the sweep voltage (V1−ΔVa) is, for example, 3.1 V, and the return voltage (V1+ΔVb) is, for example, 3.5 V. Accordingly, both the deviations ΔVa and ΔVb from the reference voltage to the sweep voltage and the return voltage are at 0.2 V.

As described above, the second voltage V2 (at 3.0 V), as generated at the intermediate node between the resistors R11, R12, is applied to the minus terminal AF− of the oxygen concentration sensor AFS so that the voltage difference (V1−V2=0.3 V) between the first voltage V1 and the second voltage V2 is applied between the two terminals of the air/fuel ratio sensor AFS. Thus, an electric current based on the oxygen concentration in the exhaust gas flows through the air/fuel ratio sensor AFS.

In the signal path between the shunt resistor R3 of the operation amplifier OP3 and the plus terminal AF+ of the oxygen concentration sensor AFS, surge absorbing and noise eliminating diodes D2, D3 are connected with the plus voltage VB side and the ground side (or minus side) of the battery power supply.

A current identical to the current I that flows through the element of the oxygen concentration sensor AFS flows through the shunt resistor R3 of the operation amplifier OP3 so that the potential difference between the two ends of the shunt resistor R3 takes a value proportional to the sensor current I. The terminal voltage Vo on the side of the oxygen concentration sensor AFS of the shunt resistor R3, i.e., the voltage Vo (V1, V1−ΔVa, or V1+ΔVb) to be applied to the plus terminal AF+ of the oxygen concentration sensor AFS is input to the input port ch11 of the sub-microcomputer 56 through an operation amplifier OPS, a resistor R4 and an input circuit 60. On the other hand, the terminal voltage Vi (i.e., a voltage according to the element current I) of the shunt resistor R3 on the side opposed to the air/fuel ratio sensor AFS is input to the input port ch12 of the sub-microcomputer 56 through an operation amplifier OP4, a resistor R5 and an input circuit 61.

The input circuit 60 on the side of the input port ch11 has a packaged operation amplifier OP6, to which the output voltage Vo of the operation amplifier OP5 is input, and the output terminal of the operation amplifier OP6 is connected with the input port ch11 through two resistors R19, R20 and with the ground through a pull-down resistor R18. The intermediate node between the two resistors R19, R20 is connected with the side of the supply voltage Vcc (e.g., 5 V) through an overvoltage protecting diode D1, and a noise eliminating capacitor C4 is connected between the input port ch11 of the resistor 20 and the ground. Here, the construction of the input circuit 61 on the side of the input port ch12 is identical to that of the input circuit 60 on the side of the input port ch11.

Figure 2:
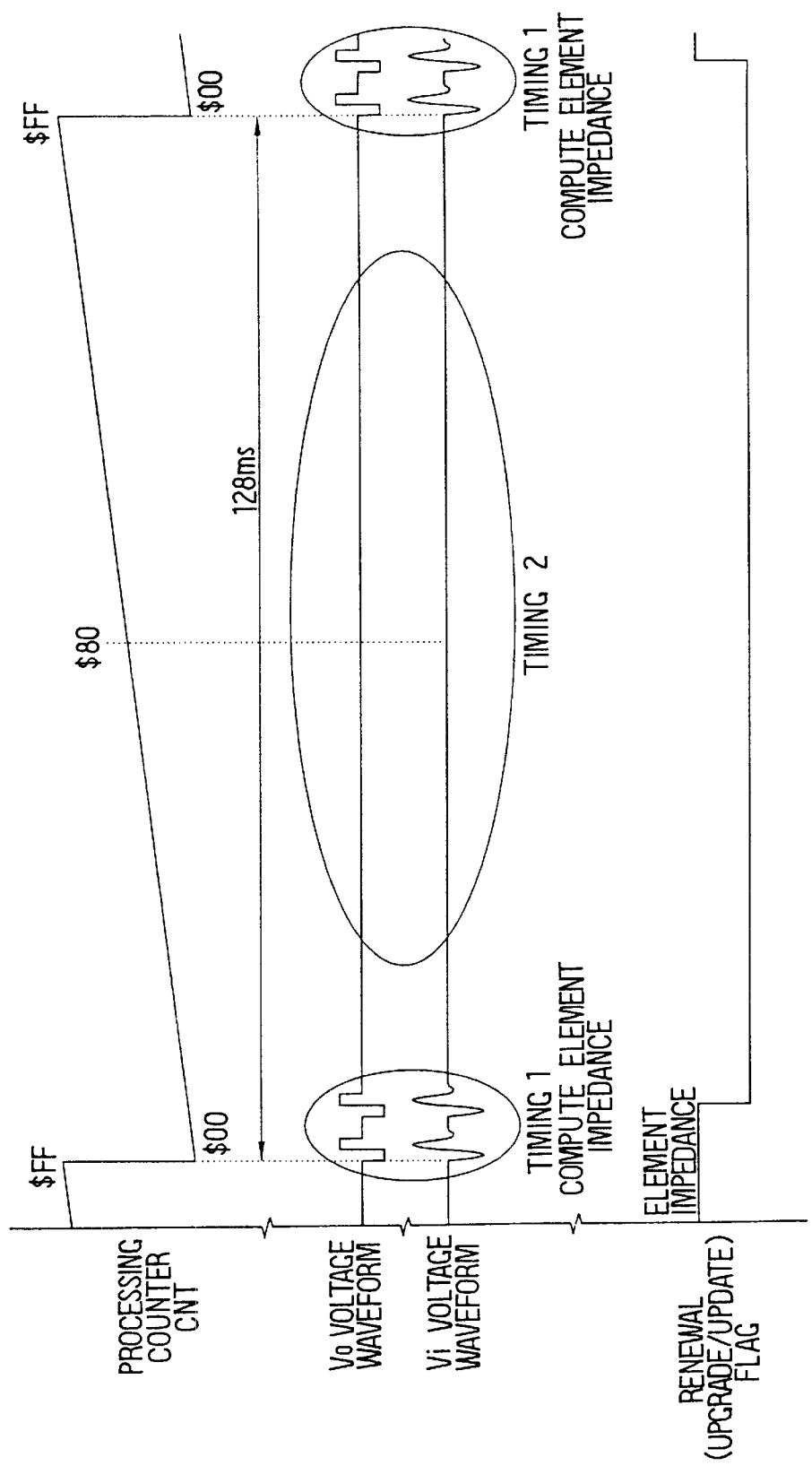
FIG. 2 is a timing diagram for explaining the summary of an element impedance detecting process of the embodiment.

A method of detecting the oxygen concentration and the element impedance will now be described. The period for detecting the oxygen concentration is set to a short period (e.g., 4 ms) to improve the detection responsibility to the change in the oxygen concentration of the exhaust gas. Considering that the change in the element temperature is more gradual than that in the oxygen concentration of the exhaust gas, the period for detecting the element impedance is set to a longer period (e.g., 128 ms), as shown in FIG. 2.

Figure 4:
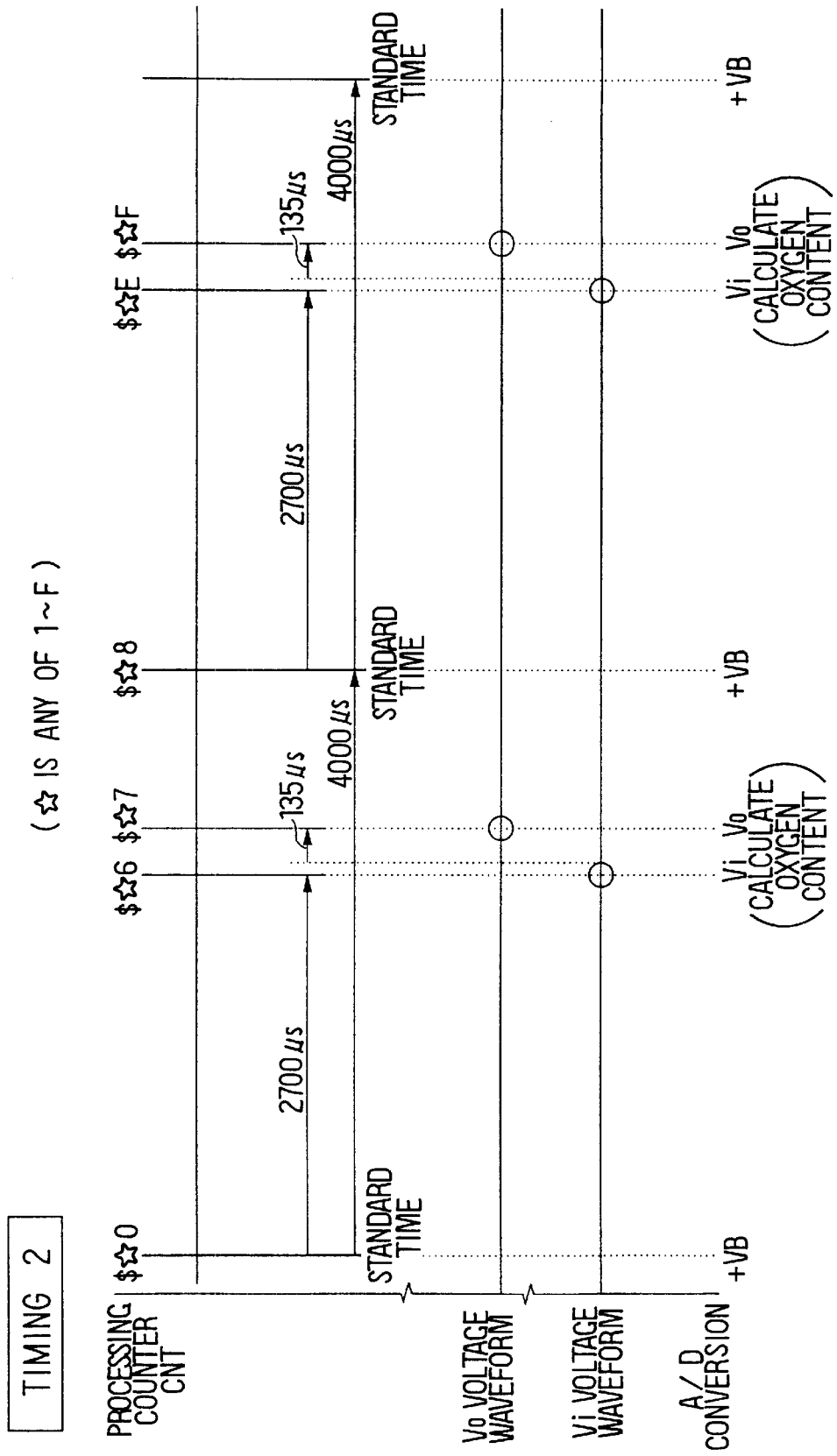
FIG. 4 is a timing diagram for explaining a process to be performed at a second timing shown in FIG. 2.

When element impedance is not being detected, as shown in FIG. 4 (i.e., during an ordinary time), the element current detecting voltage Vi and the element application voltage Vo are sequentially fetched during a period of 4 ms from the input ports ch11, ch12 of the sub-microcomputer 56 so that the oxygen concentration is computed by the sub-microcomputer 56 in the following manner. First, the element current I (or threshold current) of the oxygen concentration sensor AFS is computed by dividing the voltage difference (Vi−Vo) between the element current detecting voltage Vi and the element application voltage Vo by a resistance Rs of the shunt resistor R3:

$I=(Vi-Vo)/Rs$.

Next, the oxygen concentration map, using the element current I stored in the (not-shown) ROM of the sub-microcomputer 56, is retrieved to determine the oxygen concentration according to the present element current I.

Figure 3:
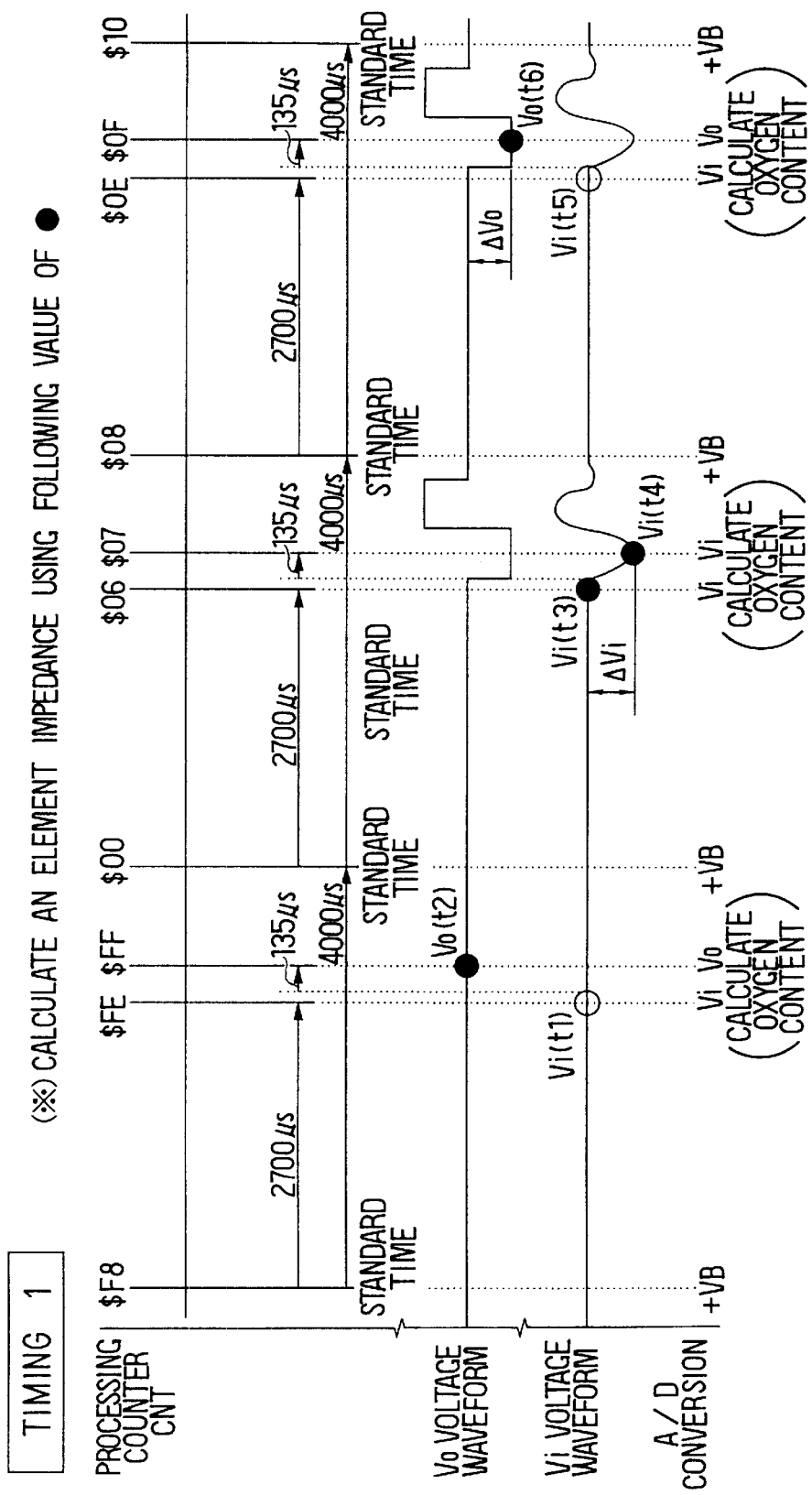
FIG. 3 is a timing diagram for explaining a process to be performed at a first timing shown in FIG. 2.

The element impedance is detected for a period of 128 ms in the following manner. For each detection of the element impedance, as shown in FIG. 2, the sweeping action to switch the element application voltage Vo from the reference voltage to the sweep voltage is executed twice. As shown in FIG. 3, moreover, for one sweep, only one of the element application voltage Vo and the element current detecting voltage Vi is subjected to an A/D conversion. On the other hand, the number and timing of A/D conversions are set to be identical i.e., two A/D conversions of Vo and Vi per 4 ms) when the element impedance is and is not to be detected. When the element current detecting voltage Vi(t4) is to be A/D converted during the sweep, moreover, the A/D conversion of the voltage Vo is skipped once, and instead the voltage Vi(t4) is A/D converted at this timing. As a result, A/D conversions of the two point voltages Vi(t3) and Vi(t4) are continuously made to detect a voltage change ΔVi according to a current change ΔI, as caused by the sweep in FIG. 3.

An element impedance Z is computed by the sub-microcomputer 56 from the following equation using the voltages Vo(t2), Vi(t3), Vi(t4) and Vo(t6), A/D converted according to the timing diagram shown in FIG. 3, and the resistance Rs of the shunt resistor R3:
[Equation 1]

$$Z = \Delta Vo / \Delta I$$
$$= \text{(Change in Element Application Voltage } Vo\text{)} /$$
$$\text{(Current at Ordinary} - \text{Current at Sweep)}$$
$$= \{Vo(t2) - Vo(t6)\} /$$
$$[(Vi(t3) - Vo(t2))/Rs - \{Vi(t4) - Vo(t6)\}/Rs]$$
$$= \{Vo(t2) - Vo(t6)\} \times Rs /$$
$$[\{Vi(t3) - Vo(t2)\} - \{Vi(t4) - Vo(t6)\}]$$
$$= \{Vo(t2) - Vo(t6)\} \times Rs /$$
$$[\{Vi(t3) - Vi(t4)\} - \{Vo(t2) - Vo(t6)\}]$$
$$= (\Delta Vo \times Rs)/(\Delta Vi - \Delta Vo),$$

wherein:
ΔVo=Vo(t2)−Vo(t6); and
ΔVi=Vi(t3)−Vi(t4).

When the element impedance Z is to be detected, on the other hand, the element current I (or oxygen concentration) is detected by using the element application voltage Vo(t2) which has been A/D converted before the sweep.

In short, at the first sweeping time, the element current I is expressed by:
I={Vi(t3)−Vo(t2)}/Rs, and at the second sweeping time, the element current I is expressed by:

$I=\{Vi(t5)-Vo(t2)\}/Rs$.

As a result, the element current I is detected once per 4 ms also at the element impedance detecting time.

In this case, when the element impedance Z and the element current I are to be detected, the timing for detecting the element application voltage Vo deviates from that for detecting the element current detecting voltage Vi. However, the element application voltage Vo is so controlled by the sensor drive circuit 59 that it may not be changed by the element current I (or oxygen concentration). Even if the timing for detecting the element application voltage Vo slightly deviates from the timing for detecting the element current detecting voltage Vi, the detection result is substantially identical to that at the instant when the element application voltage Vo is detected in the vicinity of the timing for detecting the element current detecting voltage Vi.

If the time period increases, however, the element application voltage Vo may deviate depending upon the temperature characteristics of the resistors R10–R17. Ordinarily, therefore, the element application voltage Vo is also A/D converted for a period of 4 ms together with the element current detecting voltage Vi to update the detected value of the element application voltage Vo.

Here, if the sweep voltage is switched directly to the reference voltage when the element application voltage Vo is returned after the sweep to the reference voltage, the element current I generates a peak current just after the return of the element application voltage Vo by the influence of the charge stored in a sensor element capacitive component, so that the time period for convergence to the ordinary current value is increased.

In this first embodiment, therefore, in order to converge the element current I quickly into the ordinary state after the sweep, the element application voltage Vo is switched after lapsing of the sweeping time to the return voltage, which deviates to the opposite side of the reference voltage by a value between the reference and the sweep voltages, to promote the discharge of the element capacitive component. By returning the element application voltage Vo to the reference voltage after the return voltage is held for the same time period as the sweeping time, moreover, the element application voltage Vo is returned to the reference voltage simultaneously with the end of the capacitive component discharge to converge the element current I quickly to the ordinary operating state.

Figure 5:
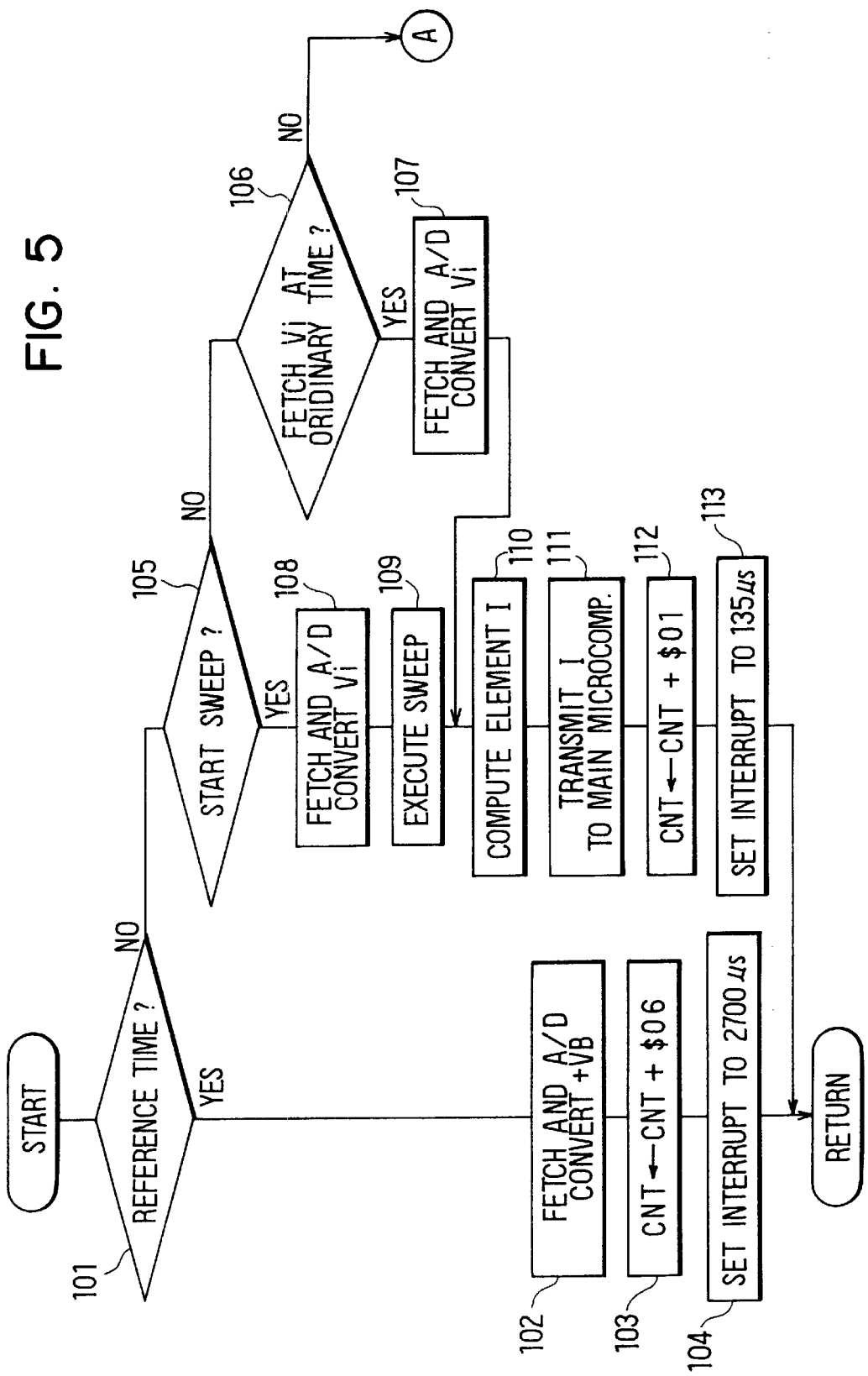
FIG. 5 is a flow diagram showing an interrupt routine of the first embodiment.

The interrupt routine, as shown in FIG. 5, is started each time an interrupt signal is generated. When this routine is started, it is decided at Step 101 in dependence upon the less significant four bits "$0" or "$8" of a process counter CNT whether or not it is the reference time. Here, the process counter CNT is an eight-digit binary counter for counting the detection period (preferably 128 ms) of the element impedance as shown in FIG. 2. This binary counter is cleared to 0 for the first sweep when the element impedance is detected, and starts a sweep for detecting a next element impedance at the instant when the process counter CNT takes a value $FF (i.e., 128 ms). Depending upon this value of the process counter CNT, the type of data to be A/D converted is decided.

When the reference time is decided at Step 101, the routine advances to Step 102, at which a battery voltage (+VB) is fetched from the input port ch1 of the sub-microcomputer 56 and is A/D converted by the A/D converter 57. At Step 103, the prevailing counted value of the process counter CNT is incremented by "$06". As a result, the value of the process counter CNT is updated to a value instructing A/D conversion of the element current detecting voltage Vi. After this, the routine advances to Step 104, at which an interrupt for fetching the element current detecting voltage Vi after 2,700 µs is set to end the routine.

When a time period of about 2,700 µs elapses, the interrupt of the routine is then restarted. In this case, the answer at Step 101 is "No", and the routine advances to Step 105, where it is decided whether or not the sweep is to be started depending on the value of the process counter CNT "$06" or "$0E". When the sweep is to be started (the answer at Step 105 is "Yes"), the routine advances to Step 108, where the element current detecting voltage Vi is fetched from the input port ch12 of the sub-microcomputer 56 and A/D converted by the A/D converter 57. At Step 109, the sweep is made to switch the element application voltage Vo from the reference voltage (at 3.3 V) to the sweep voltage (at 3.1 V).

Next, the element current I is computed at Step 110 and is transmitted to the main microcomputer 53 at Step 111. At Step 112, the prevailing counted value of the process counter CNT is incremented by "$01". As a result, the value of the process counter CNT is updated to a value instructing the next A/D conversion timing. At Step 113, an interrupt for the A/D conversion after 135 µs is set to end the routine.

When it is decided at Step 105 that the sweep is not to be started, the routine advances to Step 106, where it is decided depending on the less significant 4 bits of "$06" or "$E" of the process counter CNT whether or not the timing is for fetching the element current detecting voltage Vi. If it is decided that the timing is for fetching the element current detecting voltage Vi, the routine advances to Step 107, and the element current detecting voltage Vi is fetched from the input port ch12 of the sub-microcomputer 56. After this fetched element current detecting voltage Vi is A/D converted by the A/D converter 57, Steps 110–113 are executed to perform a series of operations from the calculation of the element current I to the setting of the interrupt, thus ending the routine.

Figure 6:
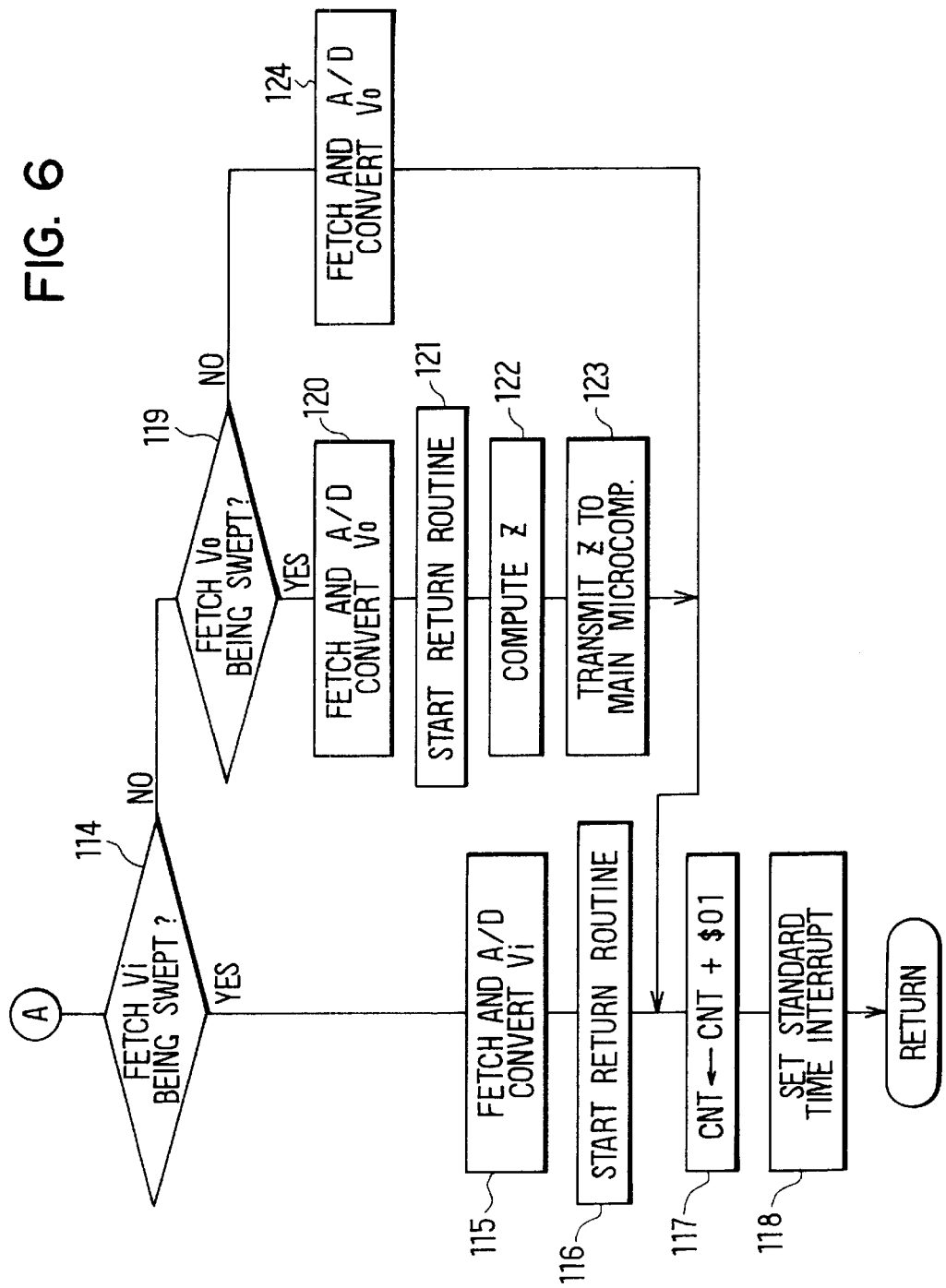
FIG. 6 is a flow diagram continuing from the diagram shown in FIG. 5.
Figure 7:
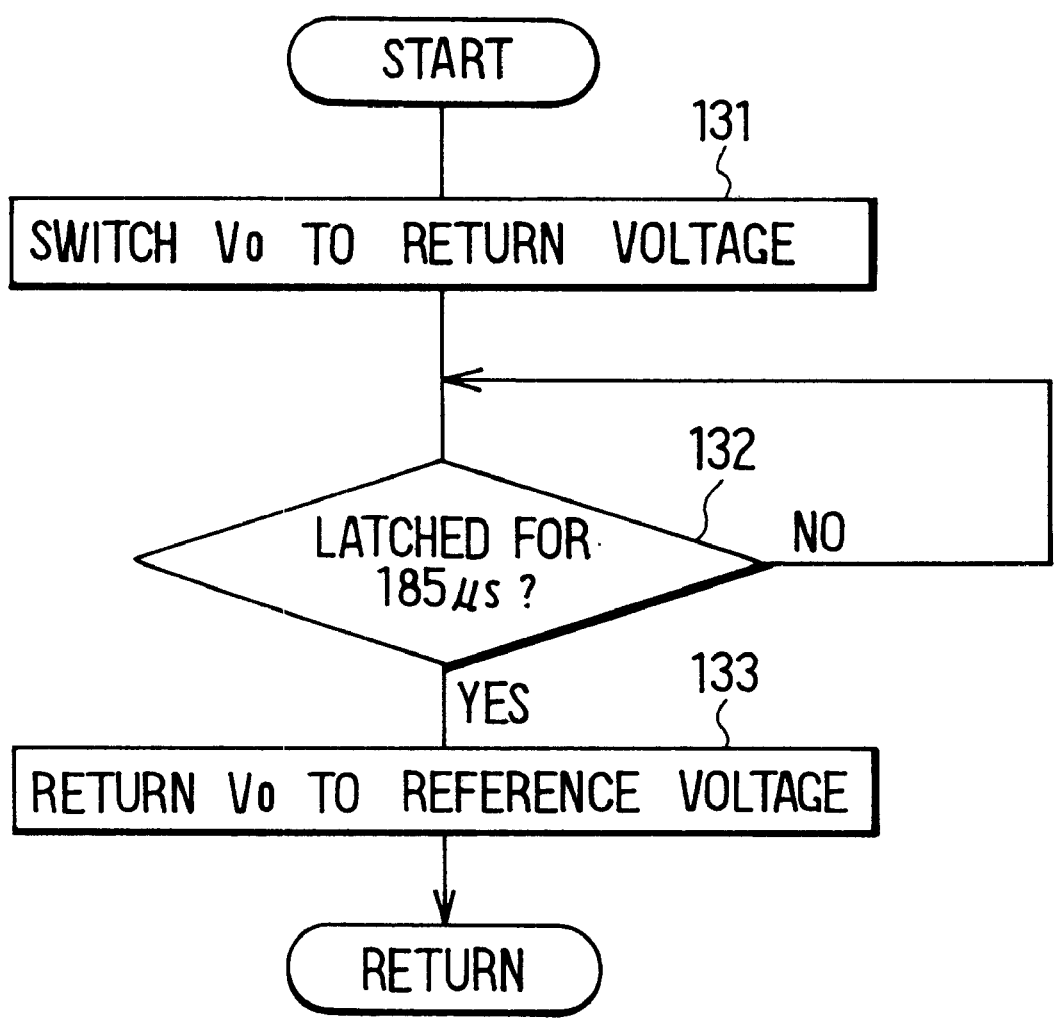
FIG. 7 is a flow diagram illustrating a return routine.

When it is decided at Step 106 that the timing is not for fetching the element current detecting voltage Vi, on the other hand, the routine advances to Step 114 of FIG. 6, where it is decided depending on the value "$07" of the process counter CNT whether or not the timing (of the first sweep) is for fetching the element current detecting voltage Vi being swept. If it is decided that the timing is for fetching the element current detecting voltage Vi being swept, the routine advances to Step 115 where the element current detecting voltage Vi is fetched from the input port ch12 of the sub-microcomputer 56 and is A/D converted by the A/D converter 57. Immediately after this A/D conversion, the routine advances to Step 116, and a return routine shown in FIG. 7 is started.

In the return routine, at Step 131, the element application voltage Vo is switched to the return voltage (at 3.5 V) which is deviated by the voltage difference between the reference voltage (at 3.3 V) and the sweep voltage (at 3.1 V) to the opposite side from the reference voltage. This return voltage is latched (at Step 132) for the same time period as the sweeping time period (e.g., 185 µs in this embodiment). After a lapse of about 185 µs, the routine then advances to Step 133, and the element application voltage Vo is returned to the reference voltage.

After the start of the return routine, the routine advances to Step 117 of FIG. 6, and the prevailing counted value of the process counter CNT is incremented by "$01". As a result, the value of the process counter CNT is updated to a value instructing the A/D conversion (of the reference time) of the next battery voltage. At Step 118, the interrupt of the reference time is set to end this routine.

When the answer of Step 114 is "No", on the other hand, the routine advances to Step 119, and it is decided depending on the value of "$0F" of the process counter CNT whether or not the timing (in the second sweep) is for fetching the element application voltage Vo being swept. If it is decided that the timing is for fetching the element application voltage Vo being swept, the routine advances to Step 120, and the element application voltage Vo is fetched from the input port ch11 of the sub-microcomputer 56 and is A/D converted by the A/D converter 57. Immediately after this A/D conversion, the routine advances to Step 121, and the aforementioned return routine of FIG. 7 is started to switch the element application voltage Vo to the return voltage. After the return voltage is latched for the same time period as the sweeping time period, the element application voltage Vo is returned to the reference voltage.

After the return routine is started, the routine advances to Step 122, and the element impedance Z is computed by using the aforementioned "Equation 1". At Step 123, this element impedance Z is transmitted to the main microcomputer 53. At Steps 117 and 118, the updating of the process counter CNT and the interrupt setting of the reference time are performed to end this routine.

If the answer of Step 119 is "No", on the other hand, it is decided that the timing is for fetching the element application voltage Vo during normal operation, and the routine advances to Step 124, at which the element application voltage Vo is fetched from the input port ch11 of the sub-microcomputer 56 and is A/D converted by the A/D converter 57. Then, at Steps 117 and 118, the updating of the process counter CNT and the interrupt setting of the reference time are performed to end this routine.

According to this first embodiment, for detecting the element impedance once, switching of the element application voltage Vo from the reference voltage to the sweep voltage is executed two times, and only one of the element application voltage Vo and the element current detecting voltage Vi is A/D converted during one sweep. As a result, the sweeping time can be made less than that of the prior art so that the oxygen concentration can be detected accurately without being influenced by the sweep, and so that the signal of another channel can also be A/D converted during the sweep. It is, however, needless to say that the invention can be modified to perform no A/D conversion of the signal of another channel during the sweep.

In this first embodiment, on the other hand, even when the element impedance is to be detected, the number and timing of A/D conversions can be set identical to those at the instant when the element impedance is not detected.

As a result, the number and timing of A/D conversions need not be switched at the time of detecting the element impedance so that A/D conversion control is facilitated.

Moreover, the A/D conversion of the element current detecting voltage Vi of two points for detecting the voltage change ΔVi according to the current change by the sweep is made continuous. As a result, the deviation of the voltage Vi due to the change in the oxygen concentration for the time period of the two points can be reduced to highly accurately detect the voltage change ΔVi according to the current change by the sweep so that the element impedance can be accurately detected.

Moreover, immediately after the A/D conversion, the element application voltage Vo is switched to the return voltage by switching the element application voltage Vo to the sweep voltage so that the sweeping time period can be set to the shortest value. After the sweep, moreover, the return voltage is latched for the same time period as the sweeping time period and then returned to the reference voltage so that the time period for latching the return voltage can be optimized to the sweeping time period to return the element application voltage Vo quickly to the reference voltage.

Here in this first embodiment, considering that the time period from the start of the sweep to the fetch of the voltage Vi or Vo is 135 µs and that the time period for the A/D conversion is 50 µs, the sweeping time period is set constant (at, for example, 185 µs). Considering that the responsiveness of the element current will change with element degradation or element temperature change, however, the time period (or the timing for starting the A/D conversion) from the sweep start to when the voltage Vi or Vo is fetched may be set variable according to the element degradation or the change in the element temperature to switch the element application voltage to the return voltage immediately after the A/D conversion of the voltage Vi or Vo. As a result, the return voltage is returned to the reference voltage after it is latched for the same time period as the sweeping time period. Thus, the sweeping time period or the A/D conversion timing can be optimized according to element degradation or element temperature change to reduce the corresponding deviation of the A/D converted value to improve the detection accuracy of the element impedance.

Even when the time period from the sweep start to the end of the A/D conversion changes, moreover, the element application voltage is switched from the sweep voltage to the return voltage immediately after the end of the A/D conversion during the sweep. Then, the sweeping time period can be automatically minimized. Therefore, the sweeping time period need not be set to a longer period due to estimating the change in the time period until the end of the A/D conversion.

Here in the example of the circuit construction shown in FIG. 1, the surge absorbing and noise eliminating elements on the side of the plus terminal AF+ of the oxygen concentration sensor AFS are exemplified by the diodes D2 and D3 for the following reasons. Specifically, the plus terminal AF+ performs the sweeping and returning actions for detecting the element impedance. Especially in this embodiment, the sweeping time period can be made shorter than that of conventional apparatuses. For example, if the surge absorbing and noise eliminating capacitors are connected with the plus terminal AF+ as in Unexamined Published Japanese Patent Application No. 9-292364, the voltage waveforms at the sweeping and returning times are rounded by the capacity (or time constant) of the capacitors so that the accuracy for detecting the element impedance drops. If the capacities of the capacitors are reduced, however, the surge absorbing and noise eliminating performances drop.

In this embodiment, therefore, surge absorption and noise elimination of the plus terminal AF+ are performed by the diodes D2, D3. As a result, the voltage waveforms at the sweeping and returning times can be prevented from being rounded, while surge absorption and noise elimination performance are maintained, to make the shortening of the sweeping time period and the improvement in the detection accuracy of the element impedance compatible.

On the other hand, the minus terminal AF- of the oxygen concentration sensor AFS is fixed at the constant voltage (at 3.0 V) to make no change in the voltage. It is, therefore, sufficient to connect a noise eliminating and surge absorbing capacitor C5 between the minus terminal AF- and ground.

Here, when the voltage to be applied to the oxygen concentration sensor AFS is turned OFF (or when the power supply is turned OFF), the voltage, as left on the side of the plus terminal AF+, is released, when it exceeds the voltage VB of the power supply being lowered, to the side of the power supply VB through the diode D2. Since the capacitor C5 is connected with the minus terminal AF- of the oxygen concentration sensor AFS, the voltage (especially, the charge voltage of the capacitor C5), as left on the minus terminal AF-, is latched for a long time at the OFF time of the power supply, if the diode D4 is not connected between the minus terminal AF- and the power supply VB. This imposes an overvoltage upon the oxygen concentration sensor AFS.

As shown in FIG. 1, to the contrary, the diode D4 is connected between the minus terminal AF- and the power supply VB so that the voltage, as left on the minus terminal AF-, can be quickly released at the OFF time of the power supply through the diode D4 to the power supply VB, thereby preventing the overvoltage from being imposed on the oxygen concentration sensor AFS. It should be appreciated that a diode may be alternatively be used instead of the capacitor C5.

A second embodiment of the present invention will now be described. In the foregoing embodiment, only one oxygen concentration sensor AFS is connected. In an engine (e.g., a V-type 6-cylinder engine or a V-type 8-cylinder engine) generally having two lines of exhaust pipes, the oxygen concentration sensor is attached to each of the exhaust pipes. In the case of an engine equipped with the two oxygen concentration sensors, therefore, it is conceivable to provide two sets of sensor circuits (i.e., circuit portions excepting the sub-microcomputer 56 and the main microcomputer 53) shown in FIG. 1 for the two oxygen concentration sensors AFS. With this construction, however, the scale of the sensor circuit is doubled as compared to the circuit shown in FIG. 1.

When the invention is to be applied to the system equipped with the two oxygen concentration sensors, therefore, the construction may be made according to a second embodiment shown in FIGS. 8–17 to minimize the circuit size.

Figure 8:
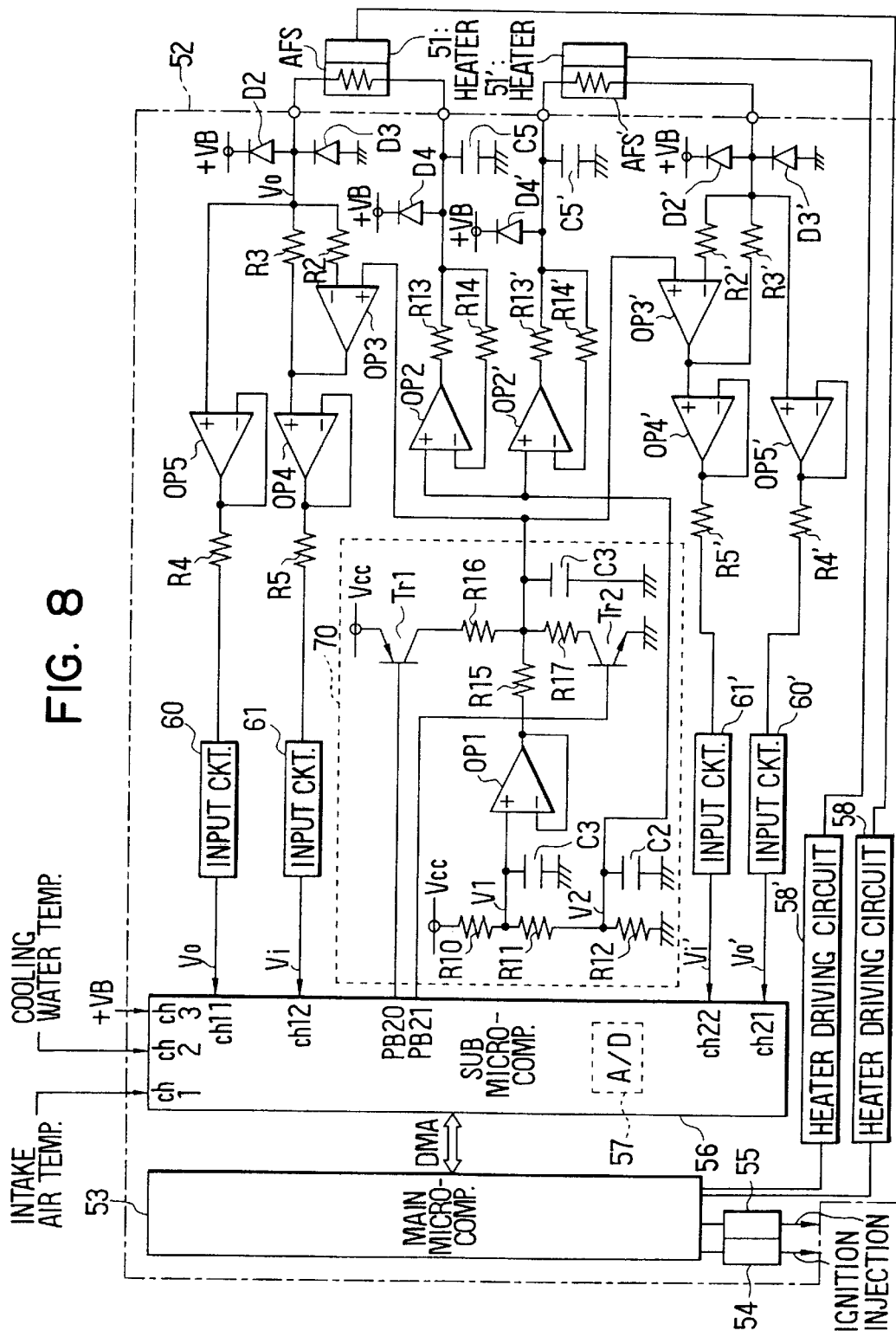
FIG. 8 is a diagram showing a circuit construction of an oxygen concentration detecting system of a second embodiment of the invention.

First, the circuit construction of this embodiment with reference to FIG. 8. In FIG. 8, the same circuit elements and the same voltage signals as those of FIG. 1 are designated by the same reference characters. On the other hand, additional circuit elements and voltage signals are designated by the reference characters which are used in FIG. 1 and "'" Here will be described the portions which are different from those of FIG. 1.

As to the sensor circuit (i.e., the circuit portion minus the sub-microcomputer 56 and the main microcomputer 53), a portion 70 (i.e., a portion for switching the element application voltages Vo, Vo') , as enclosed by dotted lines in FIG. 8, is shared between the two oxygen concentration sensors AFS, AFS', so that the voltages (or element application voltages) Vo, Vo' to be applied to the plus terminals of the two oxygen concentration sensors AFS, AFS' are simultaneously switched by switching the output voltages of the two output ports PB20, PB21 of the sub-microcomputer 56. On the other hand, the second voltage (for example 3.0 V) is applied to the minus terminals of the two oxygen concentration sensors AFS, AFS', generated in the common circuit portion 70.

Two sets of circuit portions other than the aforementioned common circuit portion 70 are provided for the two oxygen concentration sensors AFS, AFS'. Also, two input ports ch21, ch22 are added to the sub-microcomputer 56 so that the element application voltages Vo, Vo' and the element current detecting voltages Vi, Vi' of the two oxygen concentration sensors AFS, AFS' are fetched from the four input ports ch11, ch12, ch21 and ch22.

Next, the method for detecting the oxygen concentration and the element impedance of this embodiment will be described. In the following description, the element application voltage Vo, the element current detecting voltage Vi, the element impedance and the oxygen concentration (or element current) of the first oxygen concentration sensor AFS are designated by the AFS side element application voltage Vo, the AFS side element current detecting voltage Vi, the AFS side element impedance and the AFS side oxygen concentration (or AFS side element current), respectively. Also, the element application voltage Vo', the element current detecting voltage Vi', the element impedance and the oxygen concentration (or element current) of the second oxygen concentration sensor AFS' are designated by the AFS' side element application voltage Vo', the AFS' side element current detecting voltage Vi', the AFS' side element impedance and the AFS' side oxygen concentration (or AFS' side element current), respectively.

Figure 9:
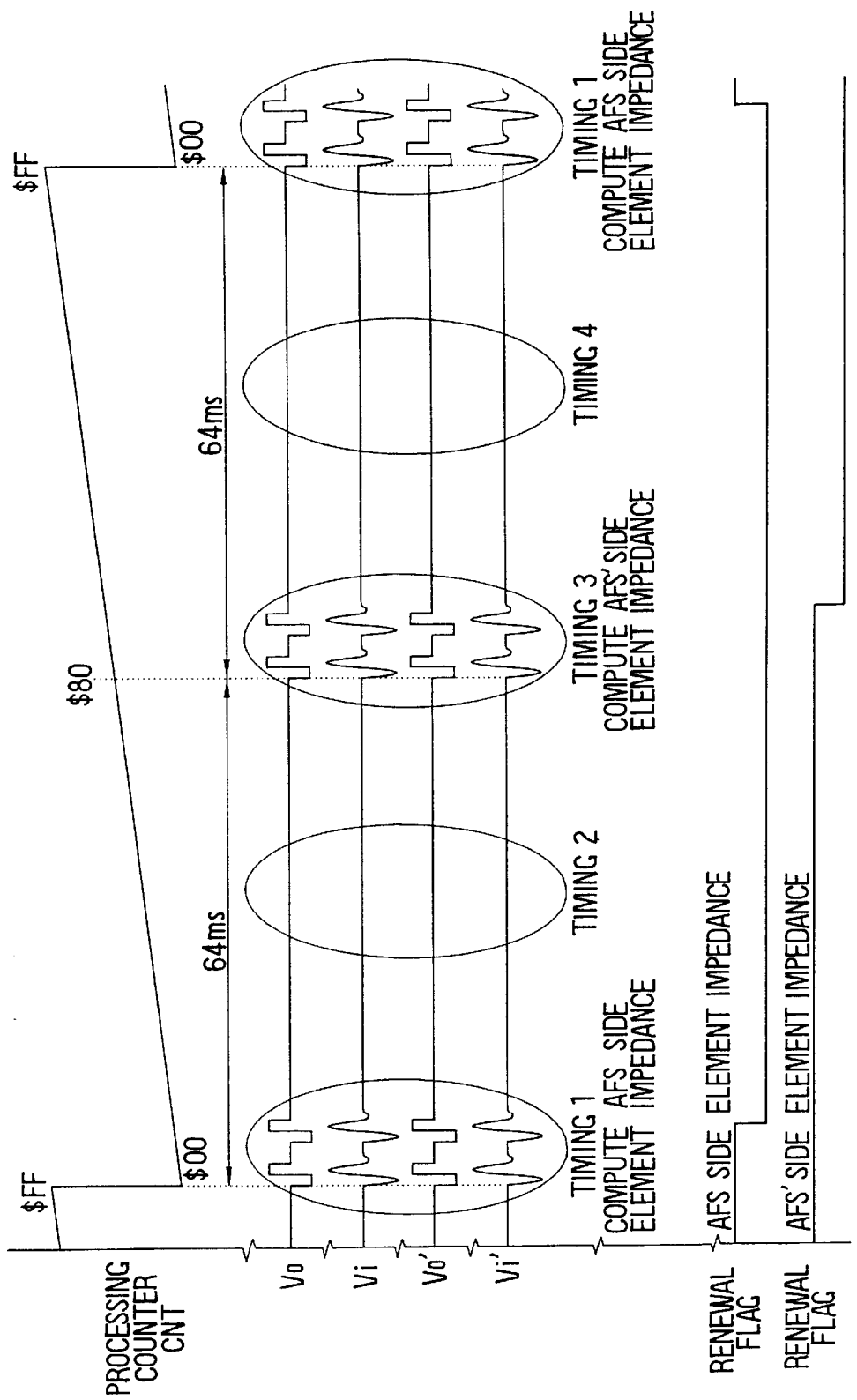
FIG. 9 is a timing diagram for explaining the summary of an element impedance detecting process of the second embodiment.

The period for detecting the oxygen concentrations of the individual oxygen concentration sensors AFS, AFS' is set to the same 4 ms, for example, as that of the foregoing embodiment, and the period for detecting the element impedances of the individual oxygen concentration sensors AFS, AFS' is set to the same 128 ms, for example, as that of the foregoing embodiment. As shown in FIG. 9, however, detection of the element impedances of the individual oxygen concentration sensors AFS and AFS' are alternately made every 64 ms, for example.

Figure 10:
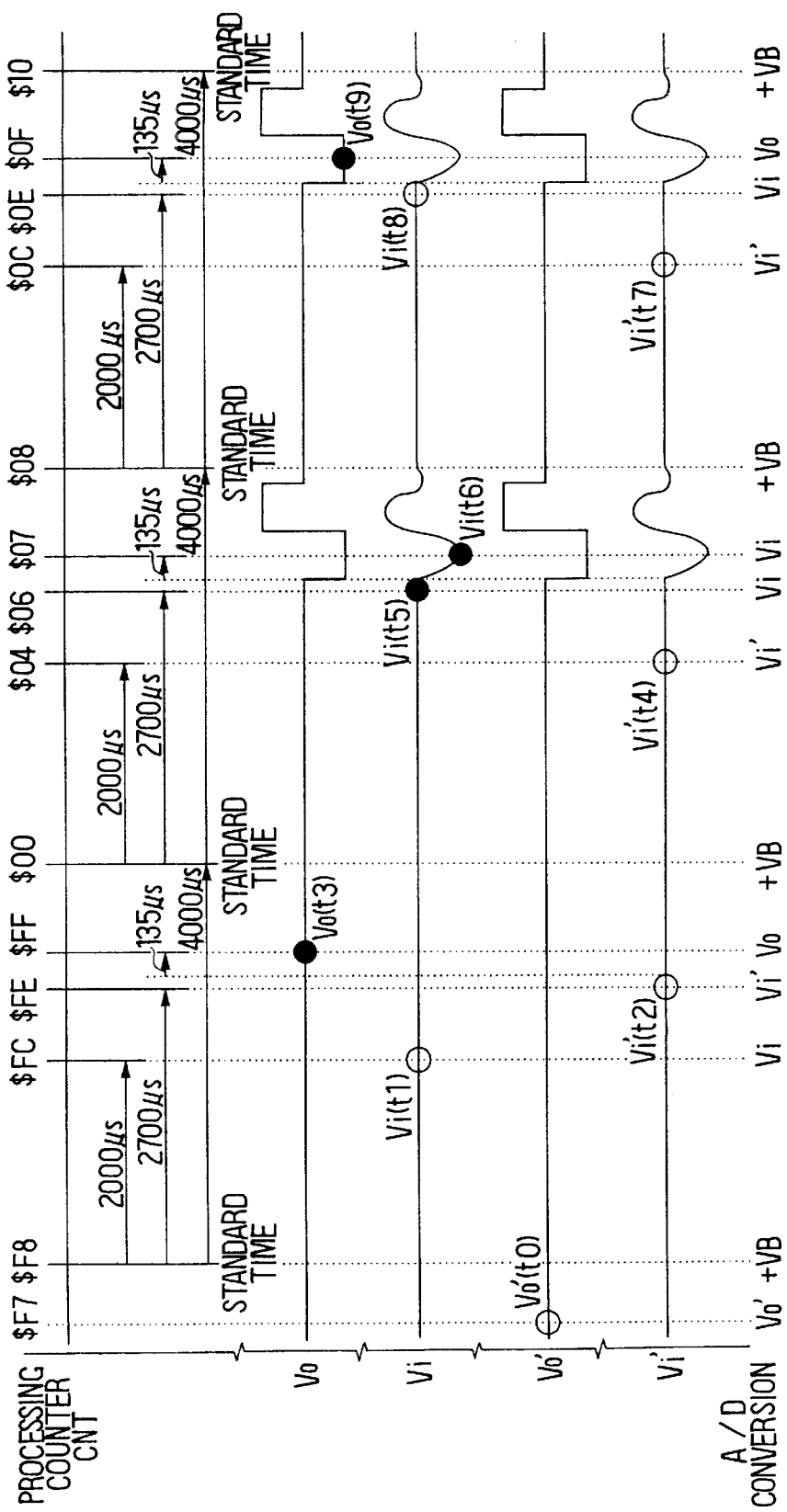
FIG. 10 is a timing diagram for explaining a process to be performed at a first timing shown in FIG. 9.

In this embodiment, therefore, two sweeps are performed for 64 ms, as shown in FIG. 9. At a timing 1 (at the time of detecting the AFS side element impedance) shown in FIG. 9, the two sweeps are executed, as shown in FIG. 10. As in the previously-described embodiment, immediately before and during the first sweep, the sequence of the A/D conversions is so interchanged (that is, the A/D conversions in the sequence of Vi→Vi' until the timing t3 but in the sequence of Vi'→Vi at and after the timing t4) that the two AFS side element current detecting voltages Vi are A/D converted consecutively twice. During the second sweep, the AFS side element application voltage Vo is A/D converted. The AFS side element impedance is computed by a method similar to that of the foregoing embodiment using Vo(t3), Vi(t5), Vi(t6) and Vo(t9) shown in FIG. 10. The AFS side element current (or oxygen concentration) is also computed once for 4 ms by a method similar to that of the first embodiment.

At this timing 1, the AFS' side element current (or oxygen concentration) is computed by using the AFS' side element application voltage Vo' (t0) every time the AFS' side element current detecting voltage Vi' is detected. More specifically, until the next AFS' side element application voltage Vo' is A/D converted at the $1F timing, the AFS' side element current is computed by using the value Vo' (t0). As described in the embodiment (1), however, no problem arises because the voltage Vo' is an invariable voltage. The AFS side element current is exemplified by the AFS side element application voltage Vo of the timing $FF as in the first embodiment.

At the timing 1 thus far described, three A/D conversions for detecting the element impedance and the oxygen concentration are executed for 4 ms.

Figure 11:
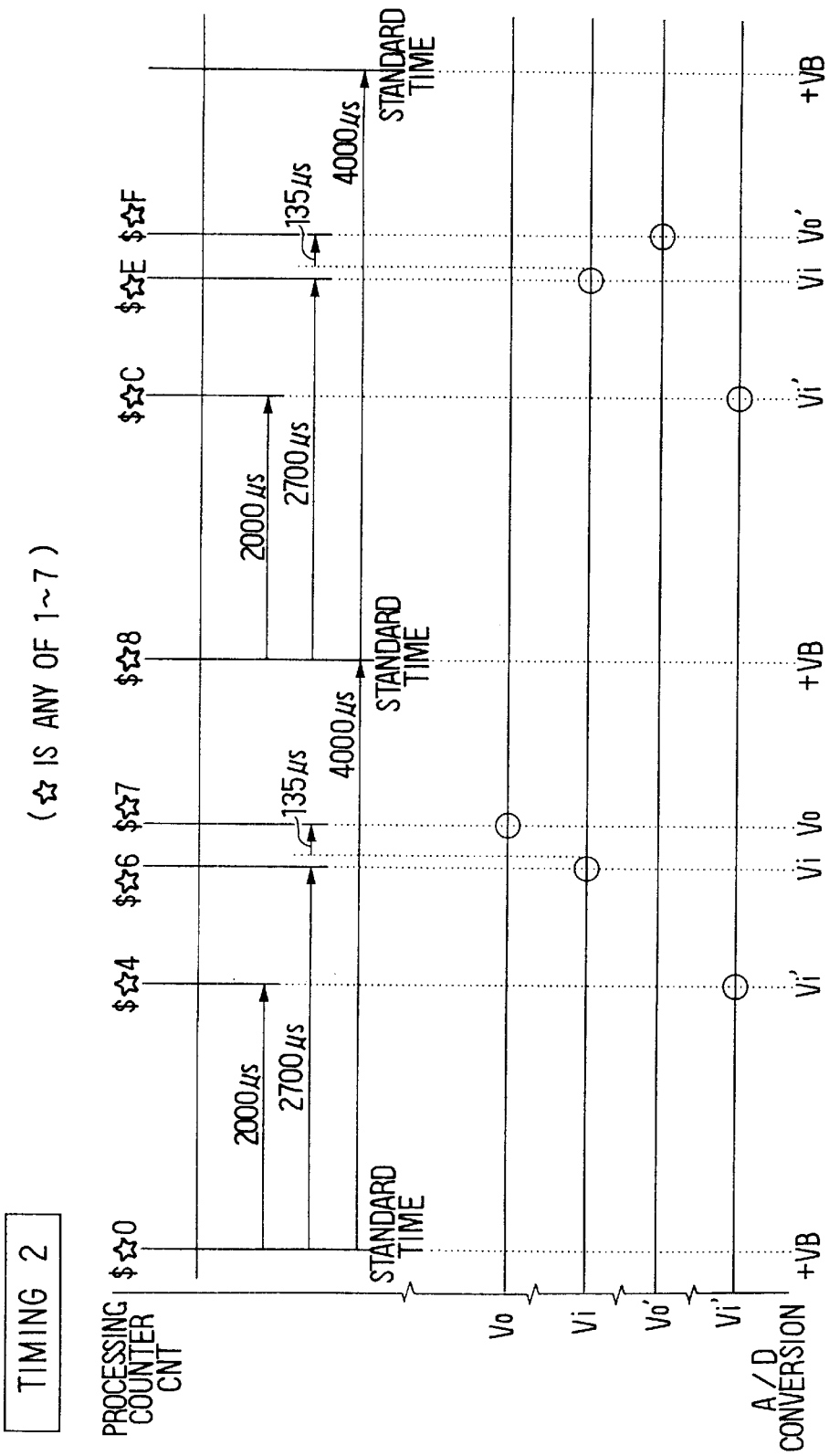
FIG. 11 is a timing diagram for explaining a process to be performed at a second timing shown in FIG. 9.

At a timing 2 (at the time ①) shown in FIG. 9, the element current detecting voltages Vi, Vi' of the two oxygen concentration sensors AFS, AFS' are sequentially A/D converted for 4 ms, as shown in FIG. 11, but the element application voltages Vo, Vo' are A/D converted for 8 ms. At this time, by shifting the A/D converting timings of the element application voltages Vo, Vo' by 4 ms from each other, three A/D conversions for detecting the oxygen concentration are also executed at the timing 2 for 4 ms as at the aforementioned timing 1. The element currents of the individual oxygen concentration sensors AFS, AFS' are computed for 4 ms by using the element application voltages Vo, Vo' which are individually A/D converted for 8 ms.

Figure 12:
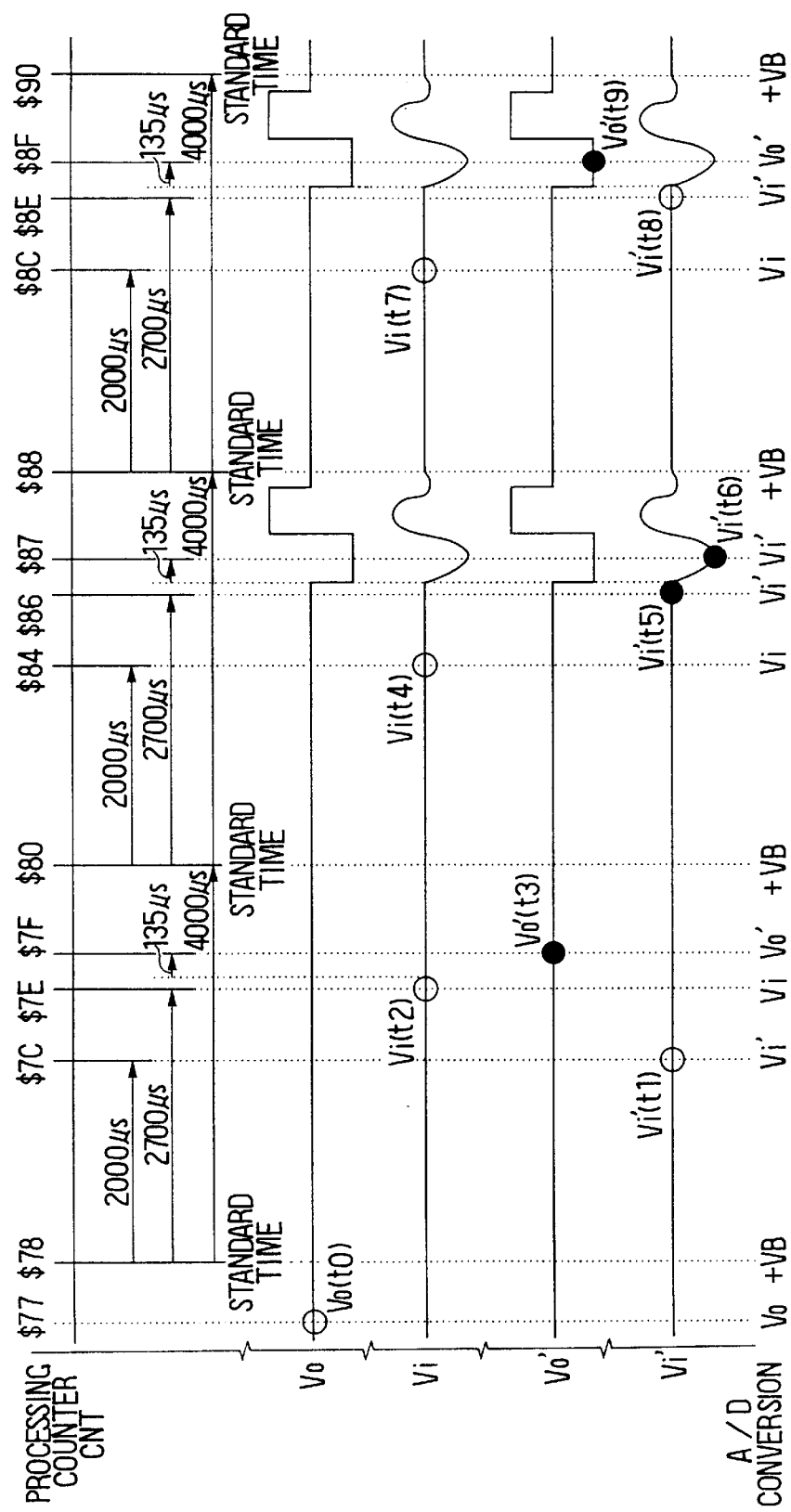
FIG. 12 is a timing diagram for explaining a process to be performed at a third timing shown in FIG. 9.

At a timing 3 (the time of detecting the AFS' side element impedance) shown in FIG. 9, the two sweeps are executed, as shown in FIG. 12. Immediately before and during the first sweep, the sequence of the A/D conversions is so interchanged (that is, the A/D conversions in the sequence of V'→Vi until the timing t3 but in the sequence of Vi→Vi' at and after the timing t4) that the two AFS' side element current detecting voltages Vi' are A/D converted consecutively by two times. During the second sweep, the AFS' side element application voltage Vo' is A/D converted. The AFS' side element impedance is computed by a method similar to that of the foregoing embodiment (1) using Vo' (t3), Vi' (t5), Vi' (t6) and Vo' (t9) shown in FIG. 12. The AFS' side element current (or oxygen concentration) is also computed once for 4 ms by a method similar to that of the embodiment (1). The AFS side element current (or oxygen concentration) is computed by using the AFS side element application voltage Vo(t0) every time the AFS side element current detecting voltage Vi is detected. At this timing 3, too, three detections of the element impedance and the oxygen concentration are executed for 4 ms as at the timing 1.

Figure 13:
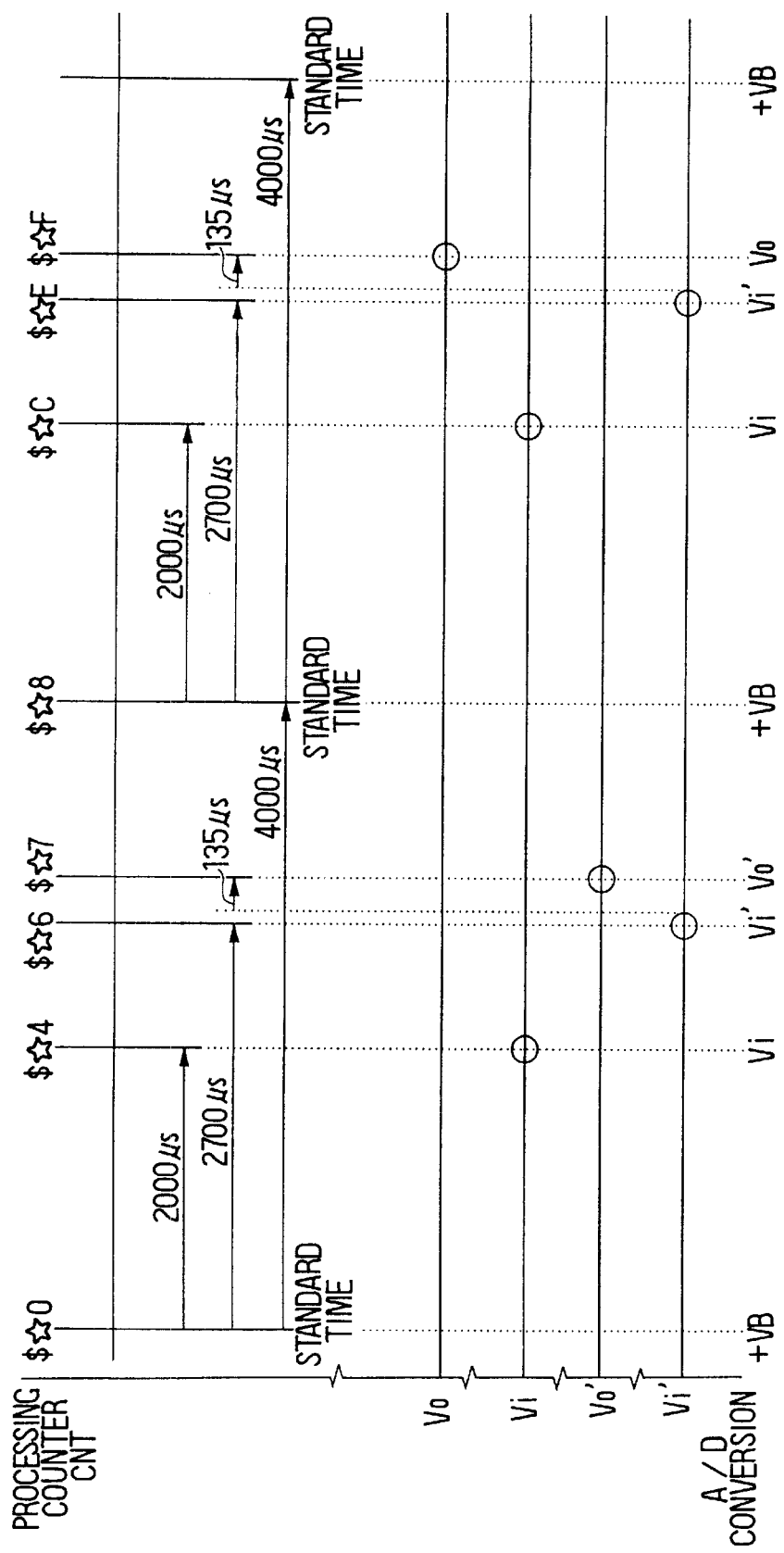
FIG. 13 is a timing diagram for explaining a process to be performed at a fourth timing shown in FIG. 9.

A timing 4 (at the time ②) shown in FIGS. 9 and 13 is different from the timing 2 (at the time ①) shown in FIG. 11 in that the sequence of the A/D conversions is interchanged. More specifically, the sequence of the A/D conversions at the timing 2 shown in FIG. 11 is:

$$+VB \rightarrow Vi' \rightarrow Vi \rightarrow Vo \rightarrow +VB \rightarrow Vi' \rightarrow Vi \rightarrow Vo'.$$

To the contrary, the sequence of the A/D conversions at the timing 4 shown in FIG. 13 is:

$$+VB \rightarrow Vi \rightarrow Vi' \rightarrow Vo' \rightarrow +VB \rightarrow Vi \rightarrow Vi' \rightarrow Vo.$$

By thus interchanging the sequence of the A/D conversions, the A/D conversions of Vi(t5), Vi(t6), Vi' (t5) and Vi' (t6) of the timing 1 and the timing 3 can be sequentially performed to reduce the influences of the sequence of the A/D conversions on the detected values of the element impedances.

Figure 14:
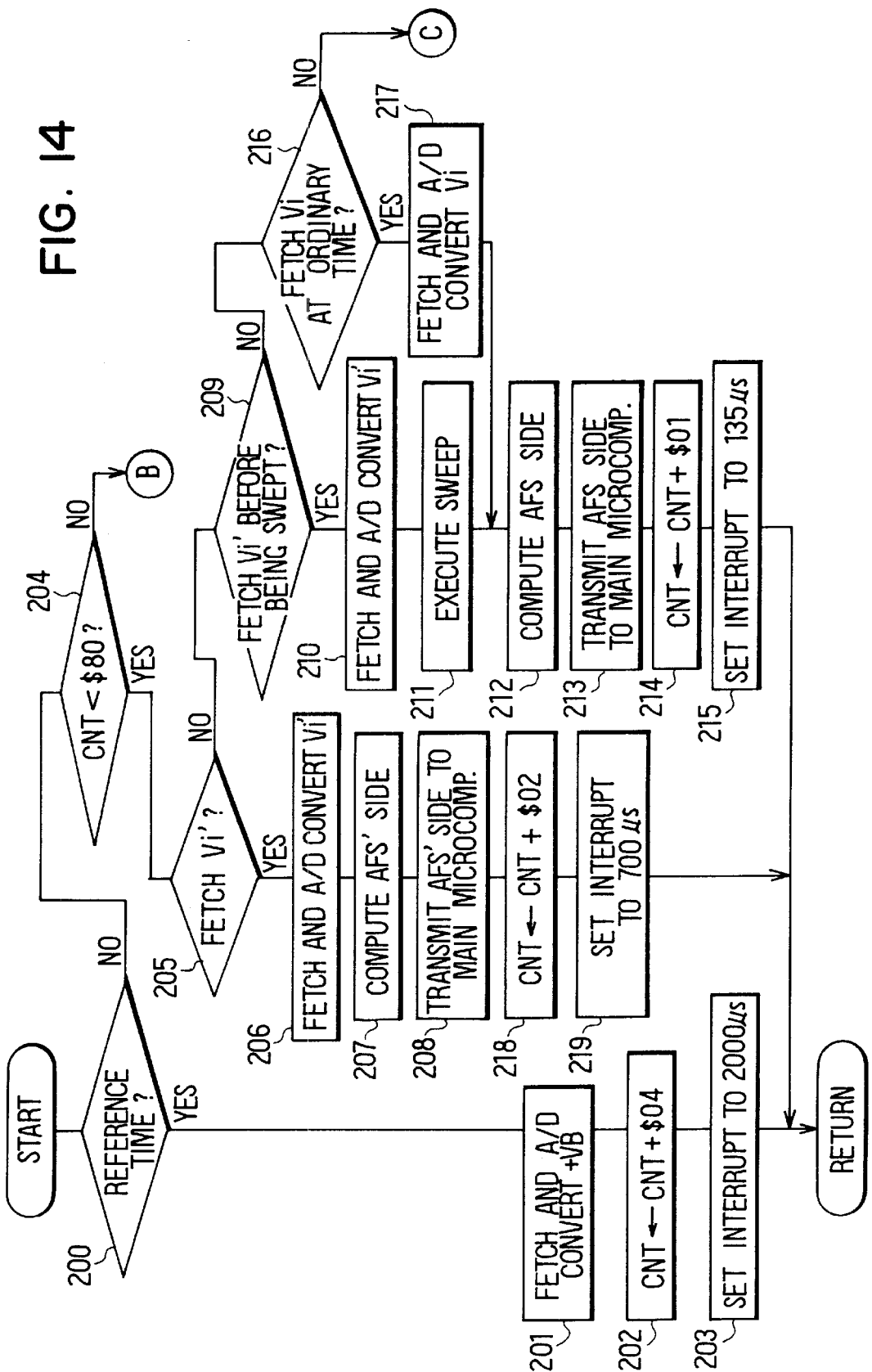
FIG. 14 is a flow diagram showing an interrupt routine of the second embodiment.

The process of this embodiment (2) thus far described is executed by the sub-microcomputer 56 according to the interrupt routine shown in FIGS. 14–17. The interrupt routine shown in FIG. 14 is started every time the interrupt signal is generated. When this routine is started, it is decided at first Step 200 whether or not it is the reference time. If at this reference time, this routine is ended by A/D converting the battery voltage (at Step 201), by adding "$04" to the value of the process counter CNT (at Step 202) and by setting an interrupt after 2,000 μs (at Step 203).

If not at the reference time, the routine advances to Step 204, at which it is decided depending upon whether the value of the process counter CNT is smaller than "$80" whether or not the prevailing process timing belongs to the aforementioned timing 1 (of FIG. 10) or the timing 2 (of FIG. 11) When it is decided that the prevailing timing belongs to the timing 1 or the timing 2, the routine advances to Step 205, and it is decided depending upon the less significant 4 bits of the process counter CNT at "$4" or "$C" whether or not the timing is for fetching the AFS' side element current detecting voltage Vi'. If this answer is "Yes", the routine advances to Step 206, and the AFS' side element current detecting voltage Vi' is fetched and is A/D converted by the A/D converter 57. Next, the routine advances to Step 207, and the AFS' side oxygen concentration (or element current) is computed. After this, at Step 208, this AFS' side oxygen concentration is transmitted to the main microcomputer 53. After this, the value "$02" is added (at Step 218) to the value of the process counter CNT. After 700 μs, an interrupt is set (at Step 219) to end this routine.

When it is decided at Step 205 that the timing is not for fetching the AFS' side element current detecting voltage Vi', on the contrary, the routine advances to Step 209, and is decided depending upon the value of the process counter CNT at "$06" or "$0E" whether or not the timing is for fetching the AFS side element current detecting voltage Vi immediately before swept. If this answer is "Yes", the routine advances to Step 210, and the AFS side element current detecting voltage Vi is fetched and is A/D converted. After this, at Step 211, there is executed a sweep for switching the element application voltages Vo, Vo' from the reference voltage (at 3.3 V) to the sweep voltage (at 3.1 V).

After this, the AFS side oxygen concentration (or element current) is computed at Step 212 and is transmitted to the main microcomputer 53 at subsequent Step 213. After this, the value "$01" is added at Step 214 to the prevailing counted value of the process counter CNT, and the routine is advanced to Step 215, and an interrupt is set after 135 μs, so that the routine is ended. When it is decided at Step 209 that the timing is not for fetching the AFS side element current detecting voltage Vi immediately before the sweep, the routine advances to Step 216, and it is decided depending upon the less significant 4 bits of the process counter CNT at "$6" or "$E" whether or not the timing is for fetching the AFS side element current detecting voltage Vi at an ordinary time (when element impedance is not being detected). If this answer is "Yes", the routine advances to Step 217, at which the AFS side element current detecting voltage Vi is fetched and is A/D converted. After this, the aforementioned operations of Steps 212–215 are executed to end this routine.

Figure 15:
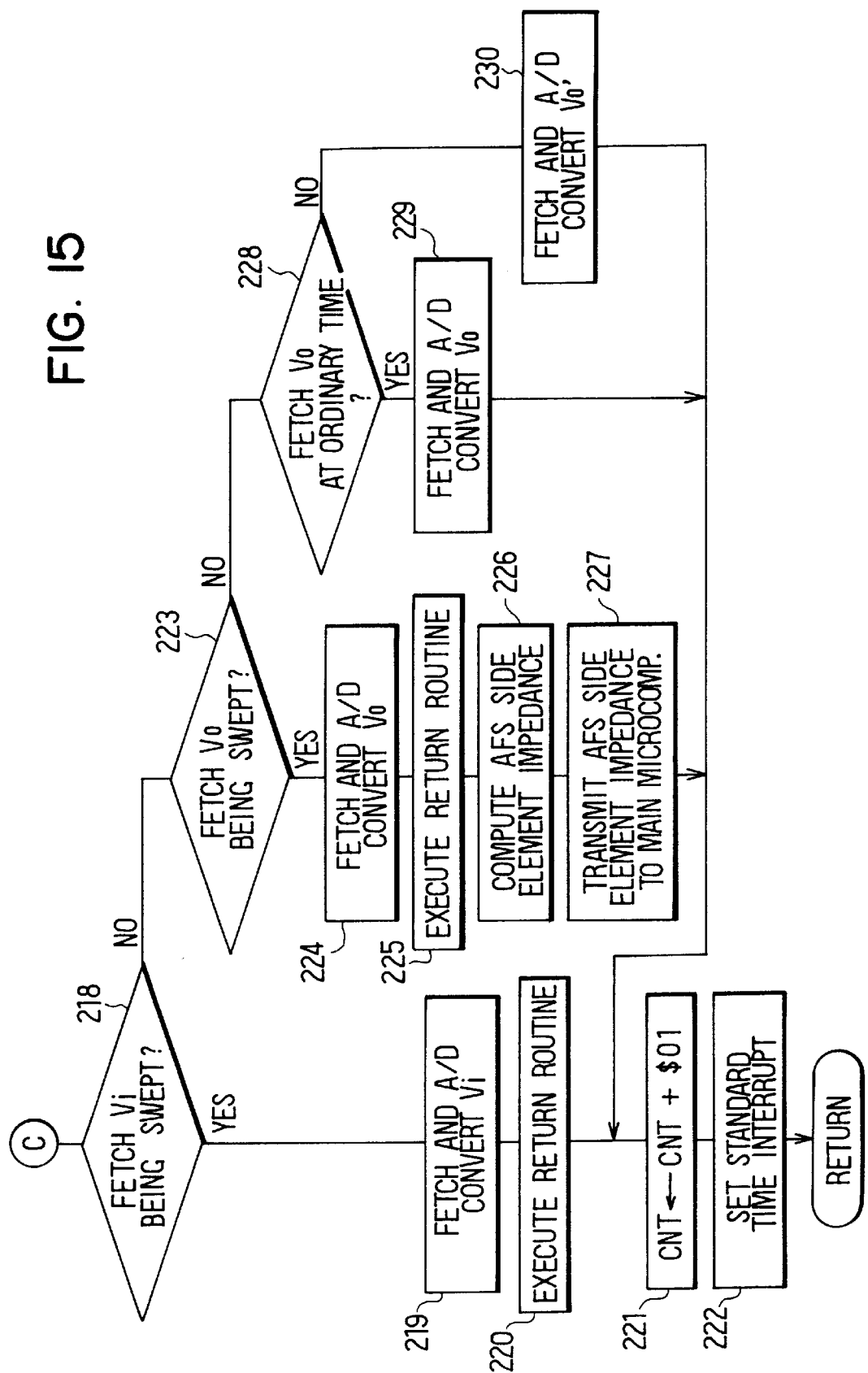
FIGS. 15 and 16 are flow diagrams continuing from the diagram shown in FIG. 14.

When it is decided at Step 216 that the timing is not for fetching the AFS side element current detecting voltage Vi at the ordinary time, on the other hand, the routine advances to Step 218 of FIG. 15, at which it is decided depending upon the value of the process counter CNT at "$07" whether or not the timing is for fetching the AFS side element current detecting voltage Vi being swept. If the answer of Step 216 is "Yes", the routine advances to Step 217, at which the AFS side element current detecting voltage Vi being swept is fetched and is A/D converted.

Immediately after this A/D conversion, the routine advances to Step 220, at which the return routine of FIG. 7 described in connection with the first embodiment is executed to switch the element application voltages Vo, Vo' from the sweep voltage (at 3.1 V) to the return voltage (at 3.5 V). This return voltage is then latched for the same time period as the sweeping time period and is then returned to the reference voltage (at 3.3 V) After the start of the return routine, the routine advances to Step 221, and the value "$01" is added to the prevailing counted value of the process counter CNT, and further to Step 222, where the interrupt of the reference time is set, so that it is ended.

When it is decided at Step 218 that the timing is not for fetching the AFS side element current detecting voltage Vi being swept, however, the routine advances to Step 223, where is decided depending upon the value of the process counter CNT at "$0F" whether or not the timing is for fetching the AFS side element application voltage Vo being swept. If it is decided that the timing is for fetching the AFS side element application voltage Vo being swept, the routine advances to Step 224, where the AFS side element application voltage Vo is fetched and is A/D converted. Immediately after this A/D conversion, the routine advances to Step 225, at which the return routine of FIG. 7 is executed to switch the element application voltages Vo, Vo' to the return voltage. After this return voltage is latched for the same time period as the sweeping time period, the element application voltages Vo, Vo' are returned to the reference voltage.

After the start of the return routine, the routine advances to Step 226, at which the AFS side element impedance is computed, and this AFS element impedance is transmitted at subsequent Step 227 to the main microcomputer 53. After this, at Steps 221 and 222, the process counter CNT is updated, and the interrupt of the reference time is set to end this routine.

When it is decided at Step 223 that the timing is not for fetching the AFS side element application voltage Vo being swept, the routine advances to Step 228, and it is decided depending upon the less significant 4 bits of the process counter CNT at "$7" whether or not the timing is for fetching the AFS side element application voltage Vo at the ordinary time. If this answer is "Yes", the routine advances to Step 229, at which time the AFS side element application voltage Vo is fetched and is A/D converted. After this, the operations of Steps 221 and 222 are executed to end this routine.

When the answer at Step 228 is "No", the routine advances to Step 230, and the AFS' side element application voltage Vo' is fetched and is A/D converted. After this, the operations of Steps 221 and 222 are executed to end this routine.

Figure 16:
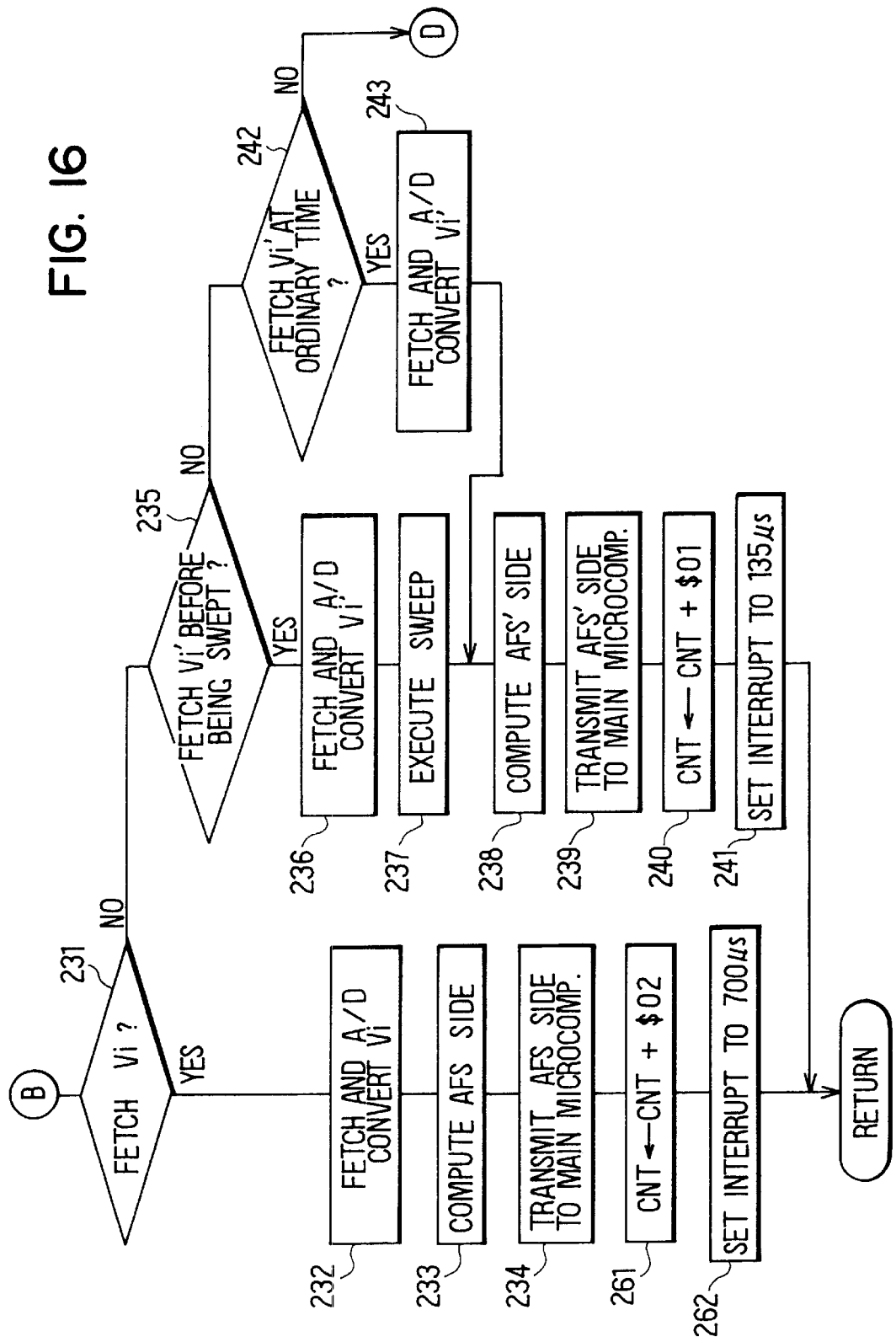

When it is decided at Step 204 of FIG. 14 that the prevailing processing timing belongs to the aforementioned timing 3 (FIG. 12) or timing 4 (FIG. 13), the routine advances to Step 231 of FIG. 16, and it is decided depending upon the less significant 4 bits of the process counter CNT at "$4" or "$C" whether or not the timing is for fetching the AFS side element current detecting voltage Vi. If this answer is "Yes", the routine advances to Step 232, and the AFS side element current detecting voltage Vi is fetched and is A/D converted. After this, at Step 233, the AFS side oxygen concentration (or element current) is computed. At Step 234, this AFS side oxygen concentration is then transmitted to the main microcomputer 53. After this, the value "$02" is added (at Step 261) to the value of the process counter CNT, and the interrupt is set (at Step 262) after 700 μs to end this routine.

When it is decided at Step 231 that the timing is not for fetching the AFS side element current detecting voltage Vi, the routine advances to Step 235, where it is decided depending upon the value of the process counter CNT at "$86" or "$8E" whether or not the timing is for fetching the AFS' side element current detecting voltage Vi' immediately before the sweep. If this answer is "Yes", the routine advances to Step 236, and the AFS' side element current detecting voltage Vi' is fetched and is A/D converted. After this, at Step 237, a sweeping operation is executed to switch the element application voltages Vo, Vo' from the reference voltage (at 3.3 V) to the sweep voltage (at 3.1 V).

After this, the AFS' side oxygen concentration (or element current) is calculated at Step 238, and this AFS' side oxygen concentration is then transmitted at Step 239 to the main microcomputer 53. After this, at Step 240, the value "$01" is added to the prevailing counted value of the process counter CNT, and the routine advances to Step 241, and the interrupt is set after 135 μs to end this routine.

When it is decided at Step 235 that the timing is not for fetching the AFS' element current detecting voltage Vi' immediately before swept, on the contrary, the routine advances to Step 242, and it is decided depending upon the less significant 4 bits of the process counter CNT at "$6" or "$E" whether or not the timing is for fetching the AFS' side element current detecting voltage Vi' at the ordinary time. If this answer is "Yes", the routine advances to Step 243, and the AFS' side element current detecting voltage Vi' is fetched and is A/D converted. After this, the operations of Steps 238–241 are executed to end this routine.

Figure 17:
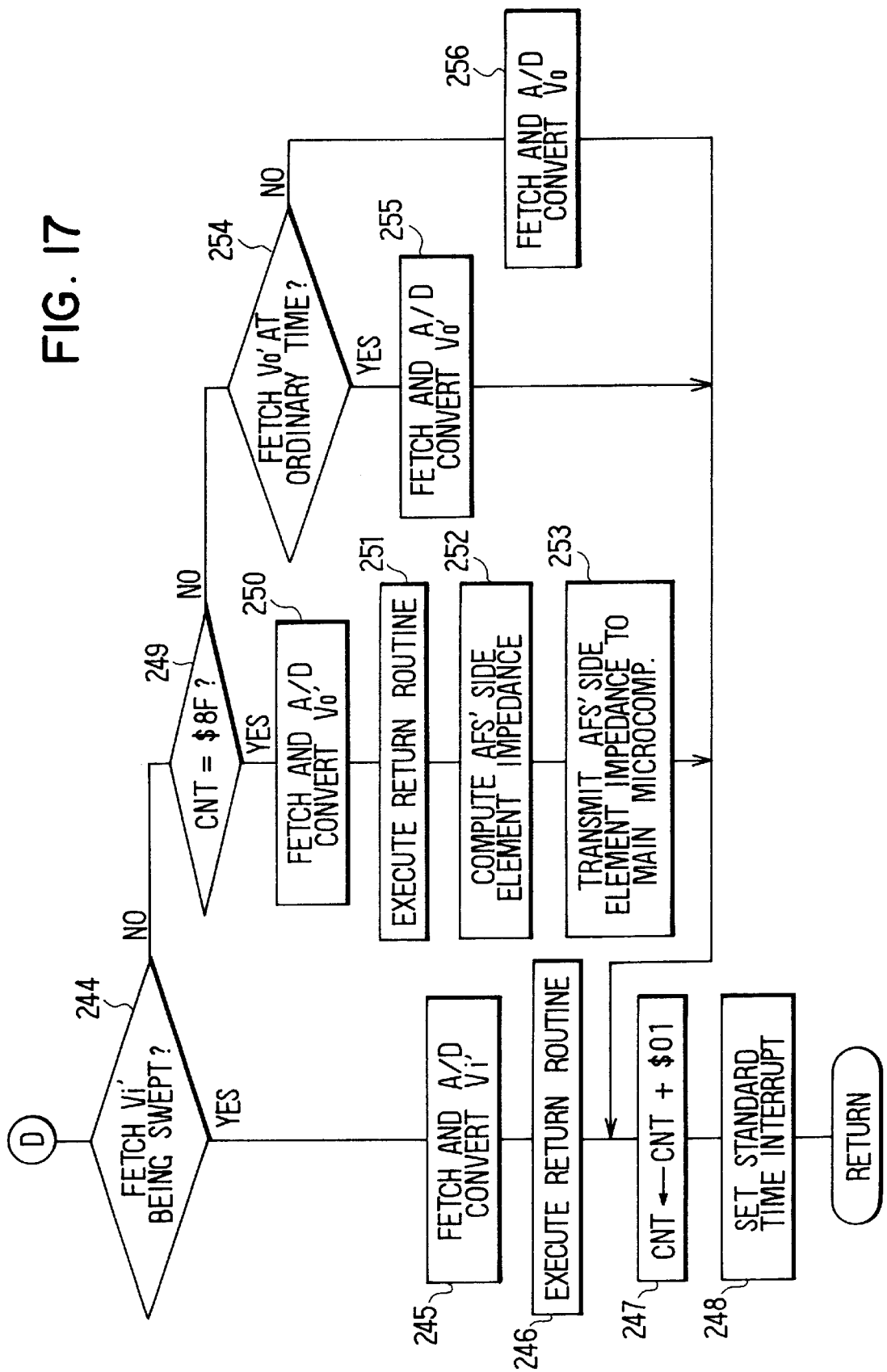
FIG. 17 is a flow diagram continuing from the flow diagram shown in FIG. 16.
Figure 18:
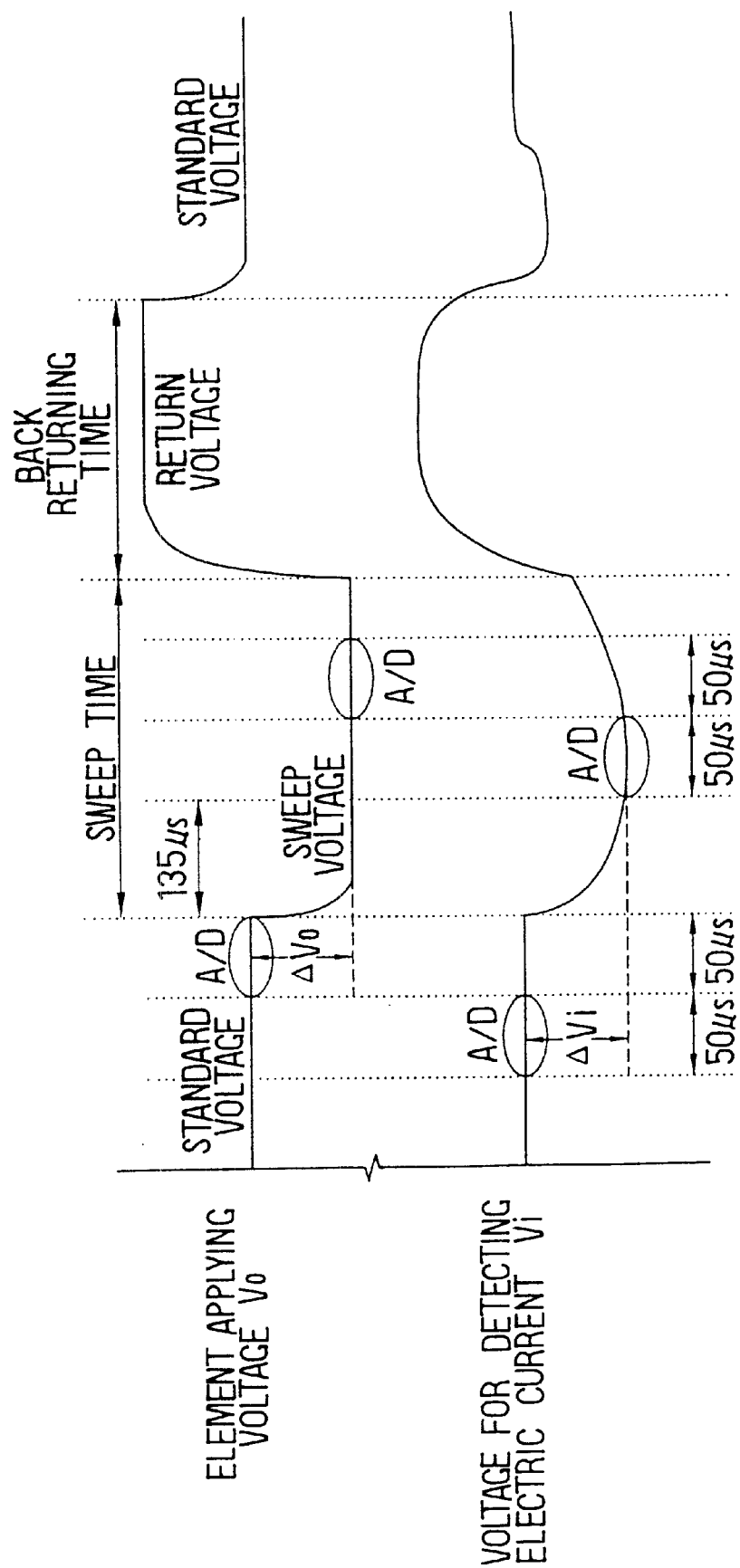
FIG. 18 is a timing diagram for explaining a conventional A/D conversion process.

When it is decided at Step 242 that the timing is not for fetching the AFS' side element current detecting voltage Vi' at the ordinary time, the routine advances to Step 244 of FIG. 17, and it is decided depending upon the value of the process counter CNT at "$87" whether or not the timing is for fetching the AFS' side element current detecting voltage Vi' being swept. If the answer at Step 244 is "Yes", the routine advances to Step 245, and the AFS' side element current detecting voltage Vi' being swept is fetched and is A/D converted.

Immediately after this A/D conversion, the routine advances to Step 246, and the aforementioned return routine of FIG. 7 is executed to switch the element application voltages Vo, Vo from the sweep voltage (at 3.1 V) to the return voltage (at 3.5 V). This return voltage is latched for the same time period as the sweeping time period and is then returned to the reference voltage (at 3.3 V). After the start of this return routine, the routine advances to Step 247, at which the value "$01" is added to the prevailing counted value of the process counter CNT. Then, the routine advances to Step 248, and the interrupt of the reference time is set to end this routine.

When it is decided at Step 244 that the timing is not for fetching the AFS' side element current detecting voltage Vi' being swept, the routine advances to Step 249, and it is decided depending upon the value of the process counter CNT at "$8F" whether or not the timing is for fetching the AFS' side element application voltage Vo' being swept. If it is decided that the timing is for fetching the AFS' side element application voltage Vo' being swept, the routine advances to Step 250, and the AFS' side element application voltage Vo' is fetched and is A/D converted. Immediately after this A/D conversion, the routine advances to Step 251, and the return routine of FIG. 7 is executed to switch the element application voltages Vo, Vo' to the return voltage. This return voltage is latched for the same time period as the sweeping time period, and the element application voltages Vo, Vo' are returned to the reference voltage.

After the start of the return routine, the routine advances to Step 252, and the AFS' element impedance is computed. After this, at Step 253, the AFS' side element impedance is transmitted to the main microcomputer 53. At Steps 247 and 248, the updating of the process counter CNT and the interrupt setting of the reference time are executed to end this routine.

If it is decided at Step 249 that the timing is not for fetching the AFS' side element application voltage Vo' being swept, the routine advances to Step 254, and it is decided depending upon the less significant 4 bits of the process counter CNT at "$7" whether or not the timing is for fetching the AFS' side element application voltage Vo' at the ordinary time. If this answer is "Yes", the routine advances to Step 255, and the AFS' side element application voltage Vo' is fetched and is A/D converted. After this, the operations of Steps 247 and 248 are executed to end this routine.

If the answer of Step 254 is "No", on the contrary, the routine advances to Step 256, and the AFS side element application voltage Vo is fetched and is A/D converted. After this, the operations of Steps 247 and 248 are executed to end this routine.

In both the first and second embodiments, the battery voltage (+VB) is fetched at the reference time, but may be replaced by another sensor output such as the cooling water temperature or the intake air temperature. At timings other than those described in the above embodiments, the A/D converter 57 is used for the A/D conversions of other sensor outputs.

In both embodiments, the transistors Tr1, Tr2 are turned ON/OFF by switching the output voltages of the output ports PB20, PB21 of the sub-microcomputer 56 to the high/low levels thereby to switch the element application voltages. However, a D/A converter may be packaged in or disposed outside of the sub-microcomputer 56 to output the element application voltages. Also, the A/D converter 57 is packaged in the sub-microcomputer 56. However, this A/D converter 57 may be disposed outside of the sub-microcomputer 56.

In both embodiments, the voltage to be applied to the plus terminal of the oxygen concentration sensor is swept at the time of detecting the element impedance. However, the applied voltage to the minus terminal may be swept. Also, not only may the element temperature is decided on the basis of the element impedance detected, but also the degradation degree or the characteristic dispersion of the oxygen concentration sensor may be evaluated.

The oxygen concentration and the element impedance are computed by the sub-microcomputer 56 in the above embodiments, but may also be computed by the main microcomputer 53. Alternatively, the functions of the main microcomputer 53 and the sub-microcomputer 56 may be performed by one microcomputer.

In the second embodiment, the AFS side element application voltage Vo and the AFS' side element application voltage Vo' are identical so that not the A/D conversion of the voltage V6 but the A/D conversion of the voltage Vo is executed even at the A/D conversion timing of the voltage Vo' to use the voltage Vo in place of the voltage Vo'. As a result, the voltage Vo' need not be fetched to the input port ch21 of the sub-microcomputer 56, and this input port ch21 can be used only for fetching another sensor output or the like.

In addition, this invention can be practiced in various manners by suitably changing the detecting period of the oxygen concentration, the detection period of the element impedance, the number of A/D conversions and the timing of A/D conversions or by suitably changing the circuit construction of the sensor drive circuit 59 or the like of the oxygen concentration detecting system 52.

While the above description constitutes the preferred embodiment of the present invention, it should be appreciated that the invention may be modified without departing from the proper scope or fair meaning of the accompanying claims. Various other advantages of the present invention will become apparent to those skilled in the art after having the benefit of studying the foregoing text and drawings in view of the following claims.

What is claimed is:

1. An impedance detecting apparatus for an oxygen concentration sensor element, said apparatus comprising:

an oxygen concentration sensor in which electric current according to oxygen concentration in a gas to be detected flows to an element having a voltage applied thereto;

a control device for switching the voltage applied to said element at a switching time from a reference voltage used for detecting oxygen concentration to a sweeping voltage used for detecting element impedance, to compute said element impedance from a voltage change $\Delta Vo$ at the switching time and a voltage change $\Delta Vi$ according to a current change caused by said voltage change $\Delta Vo$, wherein said control device switches said element application voltage from said reference voltage to said sweeping voltage at least twice for every detection of said element impedance;

an A/D converter for A/D converting said voltage applied to said element and a voltage according to said electric current, wherein said control device computes said element impedance based on an A/D conversion result of said A/D converter; and wherein said control device performs one A/D conversion on said oxygen concentration sensor during a sweeping period when said sweeping voltage is applied.

2. The apparatus of claim 1 wherein said control device successively converts voltages $V_i$ according to said current change before and after application of said sweeping voltage to compute said element impedance.

3. The apparatus of claim 1 further comprising:

wherein said A/D converter sets at least one A/D conversion timing of A/D conversions to be made a plurality of times for a predetermined time period to an identical time period independent of whether said element impedance is detected.

4. An impedance detecting apparatus for an oxygen concentration sensor element, said apparatus comprising:

an oxygen concentration sensor in which electric current according to oxygen concentration in a gas to be detected flows to an element having a voltage applied thereto; and a control device for switching the voltage applied to said element at a switching time from a reference voltage used for detecting oxygen concentration to a sweeping voltage for detecting element impedance, to compute said element impedance from a voltage change $\Delta Vo$ at the switching time and a voltage change $\Delta Vi$ according to a current change caused by said voltage change $\Delta Vo$, wherein said control device switches said element application voltage from said reference voltage to said sweeping voltage at least twice for every detection of said element impedance;

wherein said control device switches said element application voltage immediately after lapsing of a sweeping period associated with said sweeping voltage, to a return voltage which is opposite said reference voltage equal to a voltage difference between said reference and sweep voltages, to return said return voltage to said reference voltage after latching it for a time period equal to said sweeping period.

5. The apparatus of claim 4, wherein said control device performs one A/D conversion on said oxygen concentration sensor during said sweeping period.

6. The apparatus of claim 1, wherein said element impedance computing device converts two successive voltages Vi according to said current change to detect said voltage change $\Delta Vi$ due to said sweeping period.

7. An impedance detecting apparatus for an oxygen concentration sensor element, said apparatus comprising:

an oxygen concentration sensor in which electric current indicating detected gas oxygen concentration flows to a sensor element having a voltage applied to a terminal, said voltage being switched from an oxygen concentration detecting voltage to an element impedance detecting voltage to detect element impedance from (a) a voltage change $\Delta Vo$ during a sweeping period associated with said element impedance detecting voltage, and (b) a voltage change $\Delta Vi$ based on a current change caused by said voltage change $\Delta Vo$, wherein the switched terminal is connected with both plus and minus sides of a power supply through first and second diodes, respectively;

an A/D converter for A/D converting said voltage applied to said element and a voltage according to said electric current, wherein said control device computes said element impedance based on an A/D conversion result of said A/D converter; and wherein said control device performs one A/D conversion on said oxygen concentration sensor during a sweeping period when said sweeping voltage is applied.

8. An impedance detecting apparatus for an oxygen concentration sensor element, said apparatus comprising:

an oxygen concentration sensor in which electric current indicating detected gas oxygen concentration flows to a sensor element having a voltage applied to a terminal, said voltage being switched from an oxygen concentration detecting voltage to an element impedance detecting voltage to detect element impedance from (a) a voltage change $\Delta Vo$ during a sweeping period associated with said element impedance detecting voltage, and (b) a voltage change $\Delta Vi$ based on a current change caused by said voltage change $\Delta Vo$, wherein the switched terminal is connected with both plus and minus sides of a power supply through first and second diodes, respectively; and wherein said first and second diodes inhibit degradation of waveforms of said oxygen concentration detecting voltage and said element impedance detecting voltage.

9. An impedance detecting apparatus for an oxygen concentration sensor element, said apparatus comprising:

an oxygen concentration sensor in which electric current indicating detected gas oxygen concentration flows to a sensor element having a voltage applied to a terminal, said voltage being switched from an oxygen concentration detecting voltage to an element impedance detecting voltage to detect element impedance from (a) a voltage change $\Delta Vo$ during a sweeping period associated with said element impedance detecting voltage, and (b) a voltage change $\Delta Vi$ based on a current change caused by said voltage change $\Delta Vo$, wherein the switched terminal is connected with both plus and minus sides of a power supply through first and second diodes, respectively; and wherein a non-switched terminal is connected to the plus side of said power supply via a third diode and is fixed to a constant voltage.

10. An impedance detecting apparatus for an oxygen concentration sensor element, said apparatus comprising:

an oxygen concentration sensor including an element having a voltage applied thereto and in which electric current flows according to detected gas oxygen concentration; and a control device for switching the voltage applied to said element, from a reference voltage used for detecting oxygen concentration to a sweeping voltage used for detecting element impedance, to compute said element impedance from a voltage change $\Delta Vo$ at the switching time and a voltage change $\Delta Vo$ based on a current change caused by said voltage change $\Delta Vo$, wherein said control device performs, when said element impedance is once detected, at least two sweeping operations to switch said element application voltage from said reference voltage to said sweeping voltage, and detects during the first sweep the voltage change ΔVi according to a current change caused by a first sweep, and said voltage change ΔVo in at least one remaining sweep, an A/D converter for A/D converting said voltage applied to said element and a voltage according to said electric current, wherein said control device computes said element impedance based on an A/D conversion result of said A/D converter; and wherein said control device performs one A/D conversion on said oxygen concentration sensor during a sweeping period when said sweeping voltage is applied.

11. An impedance detecting apparatus for an oxygen concentration sensor element, said apparatus comprising:

an oxygen concentration sensor including an element having a voltage applied thereto and through which electric current indicative of detected gas oxygen concentration flows; and a control device for switching the voltage applied to said element, from a reference voltage used for detecting oxygen concentration to a sweeping voltage used for detecting element impedance, to compute said element impedance from a voltage change ΔVo at a time at which the voltage applied to said element is switched, and a voltage change ΔVi based on a current change caused by said voltage change Δ/Vo, wherein said control device detects said element impedance to update said element impedance value according to a predetermined time period and performs, for each said predetermined time period, at least two sweeping operations to switch said element application voltage from said reference voltage to said sweeping voltage, an A/D converter for A/D converting said voltage applied to said element and a voltage according to said electric current, wherein said control device computes said element impedance based on an A/D conversion result of said A/D converter; and wherein said control device performs one A/D conversion on said oxygen concentration sensor during a sweeping period when said sweeping voltage is applied.

12. A method for detecting the impedance of a gas concentration sensor element, said method comprising:

(i) performing one A/D conversion of a first impedance determining variable of said sensor element during a first time interval;

(ii) performing multiple A/D conversions of gas concentration detection variables of said sensor element and using same to provide gas concentration measurements during a second time interval;

(iii) performing one AID conversion of a second impedance determining variable of said sensor element during a third time interval; and using resulting data representing said first and second impedance determining variables to determine the impedance of said sensor element, said first and third time intervals being much shorter than said second time interval.

13. A method as in claim 12 wherein said second time interval is more than ten times longer than either of said first or third time intervals.

14. A method as in claim 12 wherein step (ii) is performed repeatedly at short substantially fixed intervals throughout substantially all of said second time interval.

15. Apparatus for detecting the impedance of a gas concentration sensor element, said apparatus comprising:

(i) means for performing one A/D conversion of a first impedance determining variable of said sensor element during a first time interval;

(ii) means for performing multiple A/D conversions of gas concentration detection variables of said sensor element and using same to provide gas concentration measurements during a second time interval;

(iii) means for performing one A/D conversion of a second impedance determining variable of said sensor element during a third time interval; and using resulting data representing said first and second impedance determining variables to determine the impedance of said sensor element, said first and third time intervals being much shorter than said second time interval.

16. Apparatus as in claim 15 wherein said second time interval is more than ten times longer than either of said first or third time intervals.

17. Apparatus as in claim 15 wherein said means for performing multiple A/D conversions performs such conversions repeatedly at short substantially fixed intervals throughout substantially all of said second time interval.

18. The apparatus of claim 1, wherein a number of A/D conversions set by said A/D converter for a predetermined time period is identical both when said element impedence is and is not detected.

* * * * *